(12) United States Patent
Jeung et al.

(10) Patent No.: US 9,939,130 B2
(45) Date of Patent: Apr. 10, 2018

(54) MARKER SYSTEM WITH LIGHT SOURCE

(71) Applicant: Varian Medical Systems, Inc., Palo Alto, CA (US)

(72) Inventors: Andrew G. Jeung, Mountain View, CA (US); Hassan Mostafavi, Los Altos, CA (US); George A. Zdasiuk, Portola Valley, CA (US); Gary F. Virshup, Cupertino, CA (US); Dusan Baic, Palo Alto, CA (US); Daniel R. Bilsky, San Jose, CA (US); Alexander R. Brown, San Jose, CA (US); Jon Carver, Milbrae, CA (US); Graham Faulknor, San Mateo, CA (US); Alyssa Garver, Mountain View, CA (US); Arthur Kwun, Newark, CA (US); Michelle Richmond, Palo Alto, CA (US); Josh M. Star-Lack, Palo Alto, CA (US); John G. Van Heteren, Foster City, CA (US)

(73) Assignee: Varian Medical Systems, Inc., Palo Alto, CA (US)

( * ) Notice: Subject to any disclaimer, the term of this patent is extended or adjusted under 35 U.S.C. 154(b) by 466 days.

(21) Appl. No.: 14/040,557

(22) Filed: Sep. 27, 2013

(65) Prior Publication Data

US 2014/0267773 A1    Sep. 18, 2014

Related U.S. Application Data

(60) Provisional application No. 61/798,060, filed on Mar. 15, 2013.

(51) Int. Cl.
*G06K 9/20*    (2006.01)
*F21K 99/00*    (2016.01)
(Continued)

(52) U.S. Cl.
CPC ............. *F21V 9/16* (2013.01); *A61B 5/1113* (2013.01); *A61B 5/1127* (2013.01); *A61B 90/39* (2016.02);
(Continued)

(58) Field of Classification Search
CPC .......... G06K 9/20; G02B 6/0005; F21K 9/52; F21V 9/16
(Continued)

(56) References Cited

U.S. PATENT DOCUMENTS 6,133,569 A  * 10/2000  Shoda ..................... G01J 5/061
                                                      250/330
6,662,036 B2   12/2003  Cosman
(Continued)

OTHER PUBLICATIONS

International Search Report and the Written Opinion dated Jun. 6, 2014 for related PCT Patent Application No. PCT/US2014/018359, 12 pages.

*Primary Examiner* — Andy Rao
*Assistant Examiner* — Zaihan Jiang
(74) *Attorney, Agent, or Firm* — Vista IP Law Group, LLP

(57) ABSTRACT

A marker system includes: a first marker; and a second marker; wherein the first marker and the second marker are configured to emit light from one or more light sources coupled to the first marker and the second marker; and wherein the first marker and the second marker are configured to emit the light for detection by a camera. A method performed using a marker system includes: generating light using one or more light sources; emitting the light at a plurality of markers that are coupled to the light sources; and detecting the light emitted from the plurality of markers using a camera; wherein the act of detecting comprises using one or more filters to reduce ambient light to a level that
(Continued)

corresponds with a noise level of the camera while allowing light emitted from the markers to be imaged by the camera.

53 Claims, 13 Drawing Sheets

(51) Int. Cl.
| | |
|---|---|
| *F21V 9/16* | (2006.01) |
| *F21V 8/00* | (2006.01) |
| *A61B 5/11* | (2006.01) |
| *F21K 9/61* | (2016.01) |
| *A61N 5/10* | (2006.01) |
| *A61B 17/00* | (2006.01) |
| *A61B 34/20* | (2016.01) |
| *A61B 90/00* | (2016.01) |

(52) U.S. Cl.
CPC ...... *F21K 9/61* (2016.08); *A61B 2017/00699* (2013.01); *A61B 2034/2055* (2016.02); *A61B 2090/3941* (2016.02); *A61B 2090/3945* (2016.02); *A61N 2005/1051* (2013.01); *A61N 2005/1059* (2013.01)

(58) Field of Classification Search
USPC ......... 348/169; 362/227, 231, 351, 555, 572
See application file for complete search history.

(56) References Cited

U.S. PATENT DOCUMENTS

| | | | |
|---|---|---|---|
| 6,700,613 B1* | 3/2004 | Bryant | G03B 11/00 283/88 |
| 6,980,679 B2* | 12/2005 | Jeung | A61B 5/1127 382/107 |
| 7,444,178 B2 | 10/2008 | Goldbach | |
| 7,840,256 B2 | 11/2010 | Lakin et al. | |
| 2003/0158470 A1* | 8/2003 | Wolters | A61B 1/043 600/317 |
| 2007/0134615 A1 | 6/2007 | Lovely | |
| 2007/0287342 A1* | 12/2007 | Russell | B63C 9/11 441/89 |
| 2008/0287728 A1* | 11/2008 | Mostafavi | A61N 5/1049 600/2 |
| 2009/0196401 A1* | 8/2009 | Awan | A61N 5/1042 378/150 |
| 2010/0156421 A1* | 6/2010 | Sukkau | G01R 33/3415 324/318 |
| 2010/0189659 A1* | 7/2010 | Fehre | A61K 47/48346 424/9.6 |
| 2010/0198112 A1* | 8/2010 | Maad | A61B 6/0457 600/595 |
| 2010/0200753 A1 | 8/2010 | Westaway | |
| 2011/0015521 A1* | 1/2011 | Faul | A61B 34/20 600/426 |
| 2012/0259178 A1 | 10/2012 | Kim et al. | |

* cited by examiner

MARKER SYSTEM WITH LIGHT SOURCE

RELATED APPLICATION DATA

This application claims priority to and the benefit of U.S. Provisional Patent Application No. 61/798,060, filed on Mar. 15, 2013, the entire disclosure of which is expressly incorporated by reference herein.

FIELD

An embodiment described herein relates to marker systems, and more specifically, to marker systems for use in the medical field.

BACKGROUND

Radiation therapy involves medical procedures that selectively expose certain areas of a human body, such as cancerous tumors, to high doses of radiation. The intent of the radiation therapy is to irradiate the targeted biological tissue such that the harmful tissue is destroyed. In certain types of radiotherapy, the irradiation volume can be restricted to the size and shape of the tumor or targeted tissue region to avoid inflicting unnecessary radiation damage to healthy tissue. For example, conformal therapy is a radiotherapy technique that is often employed to optimize dose distribution by conforming the treatment volume more closely to the targeted tumor.

Normal physiological movement represents a limitation in the clinical planning and delivery of conventional radiotherapy and conformal therapy. Normal physiological movement, such as respiration or heart motion, can cause a positional movement of the tumor or tissue region undergoing irradiation. If the radiation beam has been shaped to conform the treatment volume to the exact dimensions of a tumor, then movement of that tumor during treatment could result in the radiation beam not being sufficiently sized or shaped to fully cover the targeted tumoral tissue.

To address this problem, the size and/or shape of the radiation beam can be expanded by a "movement margin" (i.e., the predicted movement distance in any direction of the targeted tumor) to maintain full irradiation of the targeted tissue. The drawback to this approach is that this increased irradiation volume results in radiation being applied to otherwise healthy tissue that is located within the area of the expanded volume. In other words, motion during treatment necessitates the application of a radiation field of an expanded size that could negatively affect an unacceptably large volume of normal tissue surrounding the targeted treatment volume.

Another approach to this problem involves physiological gating of the radiation beam during treatment, with the gating signal synchronized to the movement of the patient's body. In this approach, instruments are utilized to measure the physiological state of the patient with reference to the particular physiological movement being examined. For example, respiration has been shown to cause movements in the position of a lung tumor in a patient's body. If radiotherapy is being applied to the lung tumor, then a position sensor or a strain gauge can be attached to the patient to measure the patient's respiration cycle. The radiation beam can be gated based upon certain threshold points within the measured respiratory cycle, such that the radiation beam is disengaged during periods in the respiration cycle that correspond to excessive movement of the lung tumor.

Applicant of the subject application believes that a new method and system for determining a physiological state, such as a breathing amplitude or a breathing phase, of a patient may be desirable.

SUMMARY

A marker system includes: a marker block; a first marker coupled to the marker block; and a second marker coupled to the marker block; wherein the first marker and the second marker are configured to emit light from one or more light sources physically coupled to the marker block.

Optionally, the marker system further includes a first fiber optic configured to transmit light from the one or more light sources to the first marker, and a second fiber optic configured to transmit light from the one or more light sources to the second marker.

Optionally, the marker system further includes the one or more light sources.

Optionally, the one or more light sources comprise one LED at a LED unit.

Optionally, the one or more light sources comprise a plurality of LEDs at a LED unit.

Optionally, the one or more light sources are at the marker block.

Optionally, the one or more light sources are coupled to the marker block by an optical fiber cable.

Optionally, the marker system further includes the one or more light sources.

Optionally, the one or more light sources comprise a first LED at the first marker, and a second LED at the second marker.

Optionally, one of the one or more light sources is configured to emit infrared light.

Optionally, one of the one or more light sources is configured to emit light having at least a wavelength of 365 nm.

Optionally, one of the one or more light sources is configured to emit visible light.

Optionally, one of the one or more light sources is configured to emit light having a wavelength that is anywhere from 500 nm to 700 nm.

Optionally, one of the one or more light sources has a half angle that is anywhere between 65° and 75°.

Optionally, one of the one or more light sources is configured to emit light continuously.

Optionally, one of the one or more light sources is configured to emit light in pulses.

Optionally, the first marker and the second marker are detachably coupled to the marker block.

Optionally, the marker system also includes a third marker having a third LED, and wherein the first and the third LEDs have different respective half angles, the first marker is detachably coupled to the marker block at a first location, and the third marker is detachably coupled to the marker block at the first location when the first marker is detached from the marker block.

Optionally, the marker system also includes a camera for receiving light from the first marker and light from the second marker.

Optionally, the camera comprises a first filter for reducing ambient light.

Optionally, the first filter comprises a notch filter.

Optionally, the first filter is configured to reduce the ambient light while allowing at least some of the light from the first marker and at least some of the light from the second marker to transmit therethrough.

Optionally, the first filter is configured to reduce light being imaged by the camera to a bandwidth anywhere within a range of 10 nm to 100 nm.

Optionally, the first filter comprises a bandpass filter.

Optionally, the marker system further includes one or more neutral density filters for reducing ambient light intensity.

Optionally, the camera comprises one or a combination of a bandpass filter, high pass filter, low pass filter, and neutral density filter.

Optionally, the camera comprises one or more filters for reducing ambient light to a level that corresponds with a noise level of the camera while allowing light from the first and second markers to be imaged by the camera.

A marker system includes: a first marker configured to emit light, the first marker having a first base and a first securing mechanism at the first base for detachably securing the first marker to an object; and a second marker configured to emit light, the second marker having a second base and a second securing mechanism at the second base for detachably securing the second marker to the object; wherein the first marker and the second marker are configured to emit light provided from one or more light sources that are physically coupled to the first and second markers.

Optionally, the marker system further includes a first fiber optic for providing light to the first marker, and a second fiber optic for providing light to the second marker, wherein the one or more light sources are physically coupled to the first marker via the first fiber optic, and to the second marker via the second fiber optic.

Optionally, the one or more light sources comprise a first light source and a second light source, and wherein the first marker comprises the first light source coupled to the first base, and the second marker comprises the second light source coupled to the second base.

Optionally, the marker system further includes the one or more light sources.

Optionally, the one or more light sources comprise one or more LEDs.

Optionally, one of the one or more light sources is configured to emit infrared light.

Optionally, one of the one or more light sources is configured to emit light having at least a wavelength of 365 nm.

Optionally, one of the one or more light sources is configured to emit visible light.

Optionally, one of the one or more light sources is configured to emit light having a wavelength that is anywhere from 500 nm to 700 nm.

Optionally, one of the one or more light sources has a half angle that is anywhere between 65° and 75°.

Optionally, one of the one or more light sources is configured to emit light continuously.

Optionally, one of the one or more light sources is configured to emit light in pulses.

Optionally, the first securing mechanism comprises a first adhesive and a first cover covering the first adhesive, and the second securing mechanism comprises a second adhesive and a second cover covering the second adhesive.

Optionally, the marker system further includes a camera for receiving the light emitted from the first marker and the light emitted from the second marker.

Optionally, the camera comprises a first filter for reducing ambient light.

Optionally, the first filter comprises a notch filter.

Optionally, the first filter is configured to reduce the ambient light while allowing at least some of the light from the first marker and at least some of the light from the second marker to transmit therethrough.

Optionally, the first filter is configured to reduce light being imaged by the camera to a bandwidth anywhere within a range of 10 nm to 100 nm.

Optionally, the first filter comprises a bandpass filter.

Optionally, the marker system further includes one or more neutral density filters for reducing ambient light intensity.

Optionally, the camera comprises one or a combination of a bandpass filter, high pass filter, low pass filter, and neutral density filter.

Optionally, the camera comprises one or more filters for reducing ambient light to a level that corresponds with a noise level of the camera while allowing light from the first and second markers to be imaged by the camera.

A marker system comprising: a camera configured for receiving light emitted from a first marker and light emitted from a second marker; wherein the camera comprises one or more filters for reducing ambient light to a level that corresponds with a noise level of the camera while allowing light emitted from the first and second markers to be imaged by the camera.

Optionally, light emitted from the first marker and light emitted from the second marker are generated by one or more LEDs at the first and second markers or coupled to the first and second markers by fiber optics.

Optionally, the one or more filters comprise a notch filter.

Optionally, the one or more filters are configured to reduce light being imaged by the camera to a bandwidth anywhere within a range of 10 nm to 100 nm.

Optionally, the one or more filters comprise a bandpass filter.

Optionally, the one or more filters comprise one or more neutral density filters for reducing ambient light intensity.

Optionally, the camera comprises one or a combination of a bandpass filter, high pass filter, low pass filter, and neutral density filter.

A marker system, includes: a marker block; and a plurality of markers; wherein one of the plurality of markers is configured to absorb light at a first wavelength, and emit light at a second wavelength that is different from the first wavelength.

Optionally, the one of the plurality of markers comprises a fluorescent material.

Optionally, the fluorescent material comprises a TL-0156 fluorophore.

Optionally, the one of the plurality of markers is configured to emit the light at the second wavelength in response to absorbing the light at the first wavelength.

Optionally, the marker system further includes a camera for detecting the light emitted from the one of the plurality of markers.

Optionally, the camera comprises a light source configured to emit light at the first wavelength.

A marker system, includes: a marker block; and a plurality of markers; wherein one of the plurality of markers is configured to absorb light, and to provide an afterglow in response to the absorbed light after the light is absorbed.

A marker system includes: a first marker; and a second marker; wherein the first marker and the second marker are configured to emit light from one or more light sources coupled to the first marker and the second marker; and wherein the first marker and the second marker are configured to emit the light for detection by a camera.

Optionally, the system further includes a first fiber optic configured to transmit light from the one or more light sources to the first marker, and a second fiber optic configured to transmit light from the one or more light sources to the second marker.

Optionally, the system further includes the one or more light sources.

Optionally, the one or more light sources comprise one LED at a LED unit.

Optionally, the one or more light sources comprise a plurality of LEDs at a LED unit.

Optionally, the system further includes a marker block to which the first marker and the second marker are coupled.

Optionally, the system further includes the one or more light sources, wherein the one or more light sources are at the marker block.

Optionally, the system further includes the one or more light sources, wherein the one or more light sources are external to the marker block and are coupled to the marker block by an optical fiber cable.

Optionally, the first marker and the second marker are detachably coupled to the marker block.

Optionally, the first marker comprises a first LED, and the second marker comprises a second LED; wherein the marker system further comprises a third marker having a third LED; and wherein the first and the third LEDs have different respective half angles, the first marker is detachably coupled to the marker block at a first location, and the third marker is detachably coupled to the marker block at the first location when the first marker is detached from the marker block.

Optionally, the system further includes the one or more light sources.

Optionally, the one or more light sources comprise a first LED at the first marker, and a second LED at the second marker.

Optionally, one of the one or more light sources is configured to emit infrared light.

Optionally, one of the one or more light sources is configured to emit light having at least a wavelength of 365 nm.

Optionally, one of the one or more light sources is configured to emit visible light.

Optionally, one of the one or more light sources is configured to emit light having a wavelength that is anywhere from 500 nm to 700 nm.

Optionally, one of the one or more light sources has a half angle that is anywhere between 65° and 75°.

Optionally, one of the one or more light sources is configured to emit light continuously.

Optionally, one of the one or more light sources is configured to emit light in pulses.

Optionally, the system further includes the camera for receiving light from the first marker and light from the second marker.

Optionally, the camera comprises a first filter for reducing ambient light.

Optionally, the first filter comprises a notch filter.

Optionally, the first filter is configured to reduce the ambient light while allowing at least some of the light from the first marker and at least some of the light from the second marker to transmit therethrough.

Optionally, the first filter is configured to reduce light being imaged by the camera to a bandwidth anywhere within a range of 10 nm to 100 nm.

Optionally, the first filter comprises a bandpass filter.

Optionally, the system further includes one or more neutral density filters for reducing ambient light intensity.

Optionally, the camera comprises one or a combination of a bandpass filter, high pass filter, low pass filter, and neutral density filter.

Optionally, the camera comprises one or more filters for reducing ambient light to a level that corresponds with a noise level of the camera while allowing light from the first and second markers to be imaged by the camera.

Optionally, the first marker has a first base and a first securing mechanism at the first base for detachably securing the first marker to an object; and the second marker has a second base and a second securing mechanism at the second base for detachably securing the second marker to the object.

Optionally, the first securing mechanism comprises a first adhesive and a first cover covering the first adhesive, and the second securing mechanism comprises a second adhesive and a second cover covering the second adhesive.

A marker system includes: a camera configured for receiving light emitted from a first marker and light emitted from a second marker; wherein the camera comprises one or more filters for reducing ambient light to a level that corresponds with a noise level of the camera while allowing light emitted from the first and second markers to be imaged by the camera.

Optionally, light emitted from the first marker and light emitted from the second marker are generated by one or more LEDs at the first and second markers or coupled to the first and second markers by fiber optics.

Optionally, the one or more filters comprise a notch filter.

Optionally, the one or more filters are configured to reduce light being imaged by the camera to a bandwidth anywhere within a range of 10 nm to 100 nm.

Optionally, the one or more filters comprise a bandpass filter.

Optionally, the one or more filters comprise one or more neutral density filters for reducing ambient light intensity.

Optionally, the camera comprises one or a combination of a bandpass filter, high pass filter, low pass filter, and neutral density filter.

A method performed using a marker system includes: generating light using one or more light sources; emitting the light at a plurality of markers that are coupled to the light sources; and detecting the light emitted from the plurality of markers using a camera; wherein the act of detecting comprises using one or more filters to reduce ambient light to a level that corresponds with a noise level of the camera while allowing light emitted from the markers to be imaged by the camera.

Optionally, the one or more light sources comprise one or more LEDs.

Optionally, the method further includes transmitting the generated light from the one or more light sources to the plurality of markers.

Optionally, the act of using the one or more filters comprises using a notch filter.

Optionally, the one or more filters are configured to reduce light being imaged by the camera to a bandwidth anywhere within a range of 10 nm to 100 nm.

Optionally, the act of using the one or more filters comprises using a bandpass filter.

Optionally, the act of using the one or more filters comprises using one or more neutral density filters for reducing ambient light intensity.

Optionally, the camera comprises one or a combination of a bandpass filter, high pass filter, low pass filter, and neutral density filter.

Optionally, the method further includes determining a position of an object to which the markers are coupled based at least in part on the detected light, wherein the act of determining the position is performed using a processor.

A marker system includes: a marker block; and a plurality of markers; wherein at least one of the plurality of markers is configured to absorb light at a first wavelength, and emit light at a second wavelength that is different from the first wavelength in response to absorbing the light at the first wavelength.

Optionally, the at least one of the plurality of markers comprises a fluorescent material.

Optionally, the fluorescent material comprises a TL-0156 fluorophore.

Optionally, the system further includes a camera for detecting the light emitted from the at least one of the plurality of markers.

Optionally, the camera comprises a light source configured to emit light at the first wavelength.

Optionally, at least one of the plurality of markers is configured to emit the light at the second wavelength in a form of an afterglow.

Other and further aspects and features will be evident from reading the following detailed description.

BRIEF DESCRIPTION OF THE DRAWINGS

The drawings illustrate the design and utility of various features described herein, in which similar elements are referred to by common reference numerals. These drawings are not necessarily drawn to scale. In order to better appreciate how the above-recited and other advantages and objects are obtained, a more particular description will be rendered, which are illustrated in the accompanying drawings. These drawings depict only exemplary features and are not therefore to be considered limiting in the scope of the claims.

DETAILED DESCRIPTION

Figure 1:
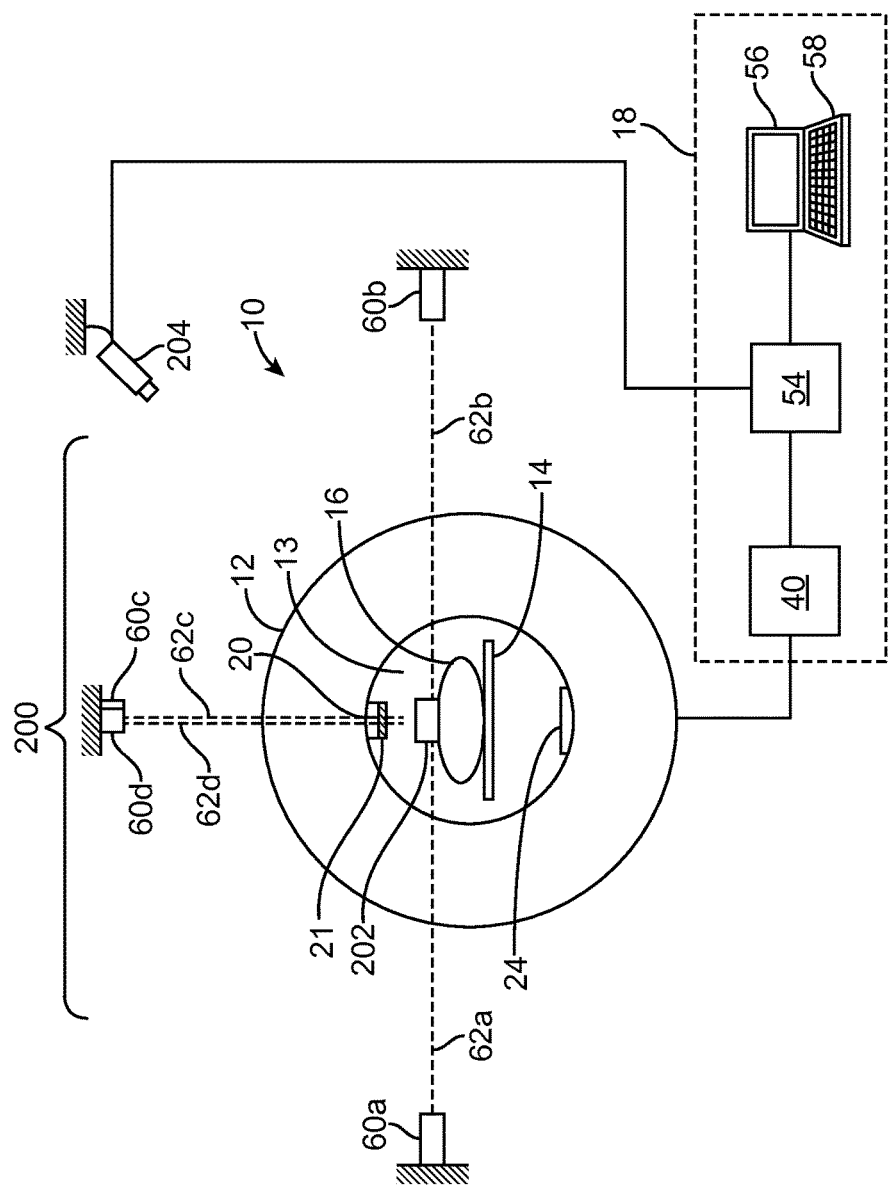
FIG. 1 illustrates a radiation system being used with a marker system.

Various features are described hereinafter with reference to the figures. It should be noted that the figures are not drawn to scale and that the elements of similar structures or functions are represented by like reference numerals throughout the figures. It should be noted that the figures are only intended to facilitate the description of the features. They are not intended as an exhaustive description of the claimed invention or as a limitation on the scope of the claimed invention. In addition, an illustrated feature needs not have all the aspects or advantages shown. An aspect or an advantage described in conjunction with a particular feature is not necessarily limited to that feature and can be practiced in any other features even if not so illustrated.

Radiation System

FIG. 1 illustrates a radiation system 10. The system 10 includes a gantry 12 having an opening (or bore) 13, a patient support 14 for supporting a patient 16, and a control system 18 for controlling an operation of the gantry 12. In the illustrated embodiments, the gantry 12 has a slip-ring configuration (donut shape). Alternatively, the gantry 12 can have other configurations, such as a C-arm configuration. The system 10 also includes a radiation source (e.g., x-ray source) 20 that projects a beam of radiation towards the patient 16, and a collimator 21 for changing a shape of the beam. The system 10 also includes a detector 24 on an opposite side of the gantry 12, which in some cases, may be used to receive radiation exiting from the patient 16, and generate image(s) using the received radiation. The detector 24 has a plurality of sensor elements configured for sensing a x-ray that passes through the patient 16. Each sensor element generates an electrical signal representative of an intensity of the x-ray beam as it passes through the patient 16. In other embodiments, the system 10 does not include the detector 24.

In the illustrated embodiments, the radiation source 20 is a treatment radiation source for providing treatment energy. In other embodiments, the radiation source 20 may be a diagnostic radiation source for providing diagnostic energy (e.g., energy that is suitable for generating an image). In further embodiments, the radiation source 20 can be configured to selectively provide treatment energy and diagnostic energy. In some embodiments, the treatment energy is generally those energies of 160 kilo-electron-volts (keV) or greater, and more typically 1 mega-electron-volts (MeV) or greater, and diagnostic energy is generally those energies below the high energy range, and more typically below 160 keV. In other embodiments, the treatment energy and the diagnostic energy can have other energy levels, and refer to energies that are used for treatment and diagnostic purposes, respectively. In some embodiments, the radiation source 20 is able to generate X-ray radiation at a plurality of photon energy levels within a range anywhere between approximately 10 keV and approximately 20 MeV.

The control system 18 includes a processor 54, such as a computer processor, coupled to a source rotation control 40. The control system 18 may also include a monitor 56 for displaying data and an input device 58, such as a keyboard or a mouse, for inputting data. During a scan to acquire x-ray projection data (e.g., cone beam CT image data), the source 20 rotates about the patient 16. The rotation of the source 20 and the operation of the radiation source 20 are controlled by the source rotation control 40, which provides power and timing signals to the radiation source 20 and controls a rotational speed and position of the source 20 based on signals received from the processor 54. Although the control 40 is shown as a separate component from the gantry 12 and the processor 54, in alternative embodiments, the control 40 can be a part of the gantry 12 or the processor 54.

In some embodiments, the system 10 may be a treatment system configured to deliver treatment radiation beam towards the patient 16 at different gantry angles. During a treatment procedure, the source 20 rotates around the patient 16 and delivers treatment radiation beam from different gantry angles towards the patient 16. While the source 20 is at different gantry angles, the collimator 21 is operated to change the shape of the beam to correspond with a shape of the target tissue structure. For example, the collimator 21 may be operated so that the shape of the beam is similar to a cross sectional shape of the target tissue structure. In another example, the collimator 21 may be operated so that different portions of the target tissue structure receive different amount of radiation (as in an IMRT procedure).

In other embodiments, the system 10 may be an imaging system. In such cases, the collimator 21 may not be needed. During a radiation imaging procedure, the radiation source 20 generates and directs an x-ray beam towards the patient 16, while the detector 24 measures the x-ray absorption at a plurality of transmission paths defined by the x-ray beam during the process. The detector 24 produces a voltage proportional to the intensity of incident x-rays, and the voltage is read and digitized for subsequent processing in a computer. After image data at different gantry angles have been collected, the collected data are processed for reconstruction of a matrix (CT image), which constitutes a depiction of a density function of the bodily section being examined. By considering one or more of such sections, a skilled diagnostician can often diagnose various bodily ailments. In some cases, the one or more sections can also be used to perform treatment planning.

As shown in the figure, the radiation system 10 is used with a marker system 200 that includes a marker block 202 and a camera 204. The camera 204 is coupled to the processor 54, which in accordance with some embodiments, may be a part of the marker system 200. Alternatively, instead of the processor 54, the camera 204 may be coupled to another processor (not shown). Also, in other embodiments, the marker system 200 may not include the camera 204. During use, the marker block 202 is coupled to the patient 16 (e.g., placed on the patient's chest, abdomen, or another body part), and the camera 204 is used to view the marker block 202. The camera 204 transmits image data to the processor 54, which processes the image data to determine a position and/or orientation of the marker block 202.

As shown in the figure, four lasers 60a-60d are positioned adjacent to the system 10. The lasers 60a-60d are configured to generate respective laser beams 62a-62d, which may be used to align the marker block 202 (and therefore, the patient 16) at a desired location. In the illustrated embodiments, lasers 60a, 60b are configured to generate and project laser beams 62a, 62b from opposite sides of the marker block 202, laser 60c is configured to generate and project laser beam 62c from above the marker block 202, and laser 60d is configured to generate and project laser beam 62d downwardly at an angle onto the marker block 202. In other embodiments, the lasers 60 may be configured to project the laser beams 62 from other directions. Each laser 60 may be mounted to any structure, such as a wall, a ceiling, a patient support, or another device. Although four lasers 60 are shown, in other embodiments, more or less than four lasers 60 may be used. For example, in other embodiments, only lasers 60a-60c are used.

Marker System

Figure 2:
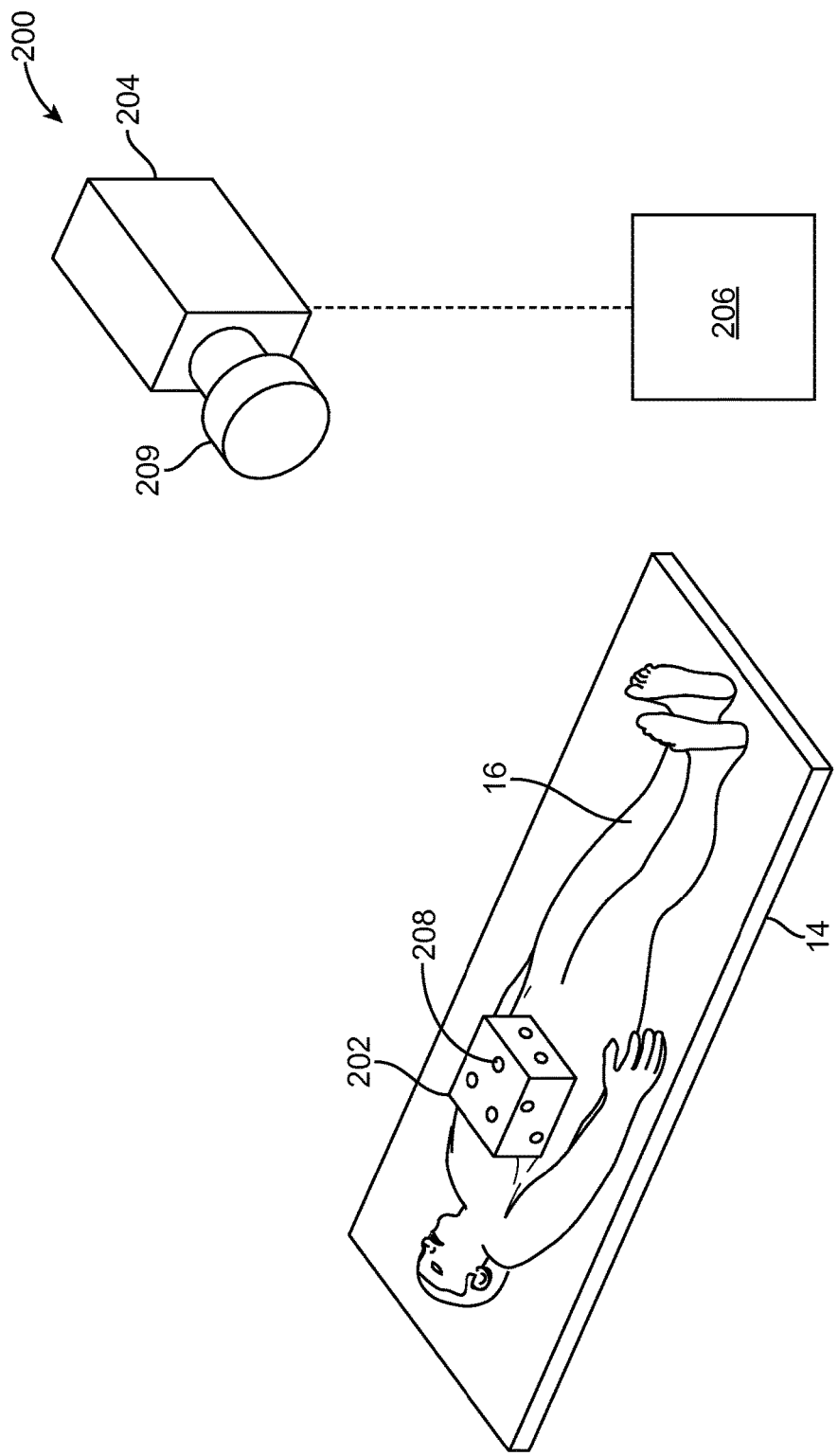
FIG. 2 illustrates a marker system.

FIG. 2 illustrates the marker system 200 of FIG. 1 in accordance with some embodiments. The marker system 200 includes the marker block 202, the camera 204, and a processing unit 206.

The marker block 202 includes a plurality of markers 208. Each marker 208 is configured to emit light. In the illustrated embodiments, each marker 208 includes a LED configured for emitting light. In some embodiments, each LED is configured to emit infrared light. In other embodiments, each LED is configured to emit visible light. In further embodiments, each LED may be configured to emit ultraviolet (UV) light. Also, in other embodiments, each LED may be configured for emitting light in different spectrums.

In some cases, each LED is configured to emit light having at least a wavelength of 890 nm (e.g., center wavelength of 890 nm). Also, in some embodiments, each LED is configured to emit light having a wavelength that is anywhere from 500 nm to 700 nm. In further embodiments, each LED is configured to emit light having a center wavelength of 365 nm.

In some embodiments, each LED has a half angle that is anywhere between 60° and 80°, and more preferably, anywhere between 65° and 75°, such as 70° (corresponding to full angle of ±70°). Each LED may be configured to emit light continuously, or in pulses. Emitting light in pulses may reduce an amount of energy required to operate the light source. In some embodiments, the markers 208 are fixedly coupled to the marker block 202. In other embodiments, the markers 208 are detachably coupled to the marker block 202. Also, in some embodiments, there may be a plurality of markers 208 with respective LEDs having different half angles. In such cases, certain markers 208 with LEDs having a desired half angle may be selectively chosen for detachably coupling to the marker block 202.

The camera 204 is configured for receiving light from the LEDs of the markers 208. In some embodiments, the camera 204 may include a filter system 209 that includes one or more filters for reducing ambient light. For example, in some embodiments, the camera 204 may include one or a combination of a notch filter, a high pass filter, a low pass filter, and a bandpass filter. In some cases, the filter(s) is configured to reduce ambient light while allowing at least some of the light from the LEDs of the markers 208 to transmit therethrough. For example, in some embodiments, the camera 204 includes one or more filters for reducing ambient light to a level that corresponds with a noise level of the camera 204 while allowing light from the LEDs of the markers 208 to be imaged by the camera 204. In further embodiments, the camera 204 may include one or more neutral density filters for reducing ambient light intensity. In still further embodiments, the camera 204 may include one or a combination of a bandpass filter, high pass filter, low pass filter, and neutral density filter. In other embodiments, the camera 204 may not include the filter system 209. For example, in other embodiments, the camera 204 may not include any notch filter, high pass filter, low pass filter, bandpass filter, and/or neutral density filter.

In some embodiments, the filter(s) may be configured to reduce light being imaged by the camera to a bandwidth anywhere within a range of 10 nm to 100 nm. Also, in some embodiments, the filter system 209 may include a narrow bandpass filter centered around the LED wavelength. For example, in some cases, the filter may have a passband of 10 nm, or any of other values. This ensures that only the LED emittance is visible in the camera image. Furthermore, in some embodiments, the filter system 209 may be configured to completely eliminate all light in the background while allowing only led light to be detected by the camera 204.

In some embodiments, the camera 204 may be a charge-couple device ("CCD") camera having one or more photoelectric cathodes and one or more CCD devices. A CCD device is a semiconductor device that can store charge in local areas, and upon appropriate control signals, transfers that charge to a readout point. When light photons from the scene to be images are focused on the photoelectric cathodes, electrons are liberated in proportion to light intensity received at the camera. The electrons are captured in charge buckets located within the CCD device. The distribution of captured electrons in the charge buckets represents the image received at the camera. The CCD transfers these electrons to an analog-to-digital converter. The output of the analog-to-digital converter is sent to processing unit 206 to process the video image and to calculate the positions of the markers 208. In other embodiments, the camera 204 may be other types of imaging device. For example, in other embodiments, the camera 204 may be a CMOS camera.

As shown in FIG. 2, the processing unit 206 is communicatively coupled to the camera 204. In some embodiments, the processing unit 206 may be the processor 54 of FIG. 1. In other embodiments, the processing unit 206 may be a component of the processor 54 of FIG. 1, or another component that is communicatively coupled to the processor 54 of FIG. 1. The processing unit 206 may include hardware, software, or combination of both. Also, in some embodiments, the processing unit 206 may include a non-transitory medium for storing data. By means of non-limiting examples, the data may be image data captured by the camera 204, processed image data, and meta data of the image data. The processing unit 206 may be communicatively coupled to the camera 204 via a cable. In other embodiments, the processing unit 206 may be communicatively coupled to the camera via a wireless network.

In operation, the marker block 202 is coupled to the patient 16. The marker block 202 may be placed on the patient 16, and/or may be secured to the patient 16 may a securing mechanism (e.g., adhesive, strap, clip, etc.). The LEDs of the markers 208 are then switched on, and as a result, light is emitted from the markers 208. In some embodiments, the marker block 202 includes a battery for providing power to energize the LEDs, and a switch for switching the LEDs on. The light from the LEDs of the markers 208 indicates the position of the markers 208. The camera 204, which is directed at patient 16, capture and detect the light emitted from the markers 208. The filter system 209 at the camera 204 filters out at least some of the ambient light while allowing light from the LEDs of the markers 208 to be captured by the camera 204. For example, the filter system 209 may reduce ambient light to a level that corresponds with a noise level of the camera 204 while allowing light from the LEDs of the markers 208 to be imaged by the camera 204. It should be noted that emitting light from the markers 208 for detection by the camera 204 is advantageous over markers that are reflectors configured to reflect light emitted from a camera. This is because emitting light from the markers 208 does not require a flood of light to illuminate towards the patient from the direction of the camera 204. Also, the detection of the markers 208 is more efficient.

The camera 204 generates video images that show the position of the markers 208 within its video frame. The video images contain mainly images of the LEDs and nothing else (or almost nothing else) in the field of view of the camera 204. The generated video images are sent to processing unit 206 (or another processor) for further processing.

The processing unit 206 (or another processor) receives video images from the camera 204. The processing unit 206 first processes each video image from the camera 204 to identify images of the markers 208 in the image frame. Based on the determined position of the markers 208, and the known relative positions among the markers 208, the processing unit 206 then determines the position (X, Y, Z) and/or orientation ($\theta_X$, $\theta_Y$, $\theta_Z$) of the marker block 202. In some embodiments, information regarding the location and orientation of the camera 204 is provided to the processing unit 206 to facilitate the computations of the position and/or orientation of the marker block 202.

A possible inefficiency in tracking the markers 208 is that the markers 208 may appear anywhere on the video frame, and all of the image elements of the video frame may have to be examined to determine the location of the markers 208. Thus, in an embodiment, the initial determination of locations for the markers 208 involves an examination of all of the image elements in the video frame. If the video frame comprises 640 by 480 image elements, then all 307200 (640*480) image elements are initially examined to find the location of the markers 208.

For real-time tracking of the markers 208, examining every image element for every video frame to determine the location of the markers 208 in real-time could consume a significant amount of system resources. Thus, in an embodiment, the real-time tracking of the markers 208 can be facilitated by processing a small region of the video frame, referred to herein as "tracking gate", that is placed based on estimation of the locations of the already-identified markers 208 in the video frame. The previously determined location of a marker 208 is used to define an initial search range (i.e., the tracking gate) for that same marker in real-time. The tracking gate is a relatively small portion of the video frame that is centered at the previous location of the marker 208. The tracking gate is expanded only if it does not contain the new location of the marker 208. As an example, consider the situation when the previously determined location of a particular marker is image element (50,50) in a video frame. If the tracking gate is limited to a 50 by 50 area of the video frame, then the tracking gate for this example would comprise the image elements bound within the area defined by the coordinates (25,50), (75,50), (50,25), and (50,75). The other portions of the video frame are searched only if the marker 208 is not found within this tracking gate.

In other embodiments, there may be multiple tracking gates for multiple respective markers, or for multiple respective sets of markers (wherein a set may include one or more markers).

In some embodiments, the determined position and/or orientation of the marker block 202 can then be used to position the patient 16 at desired position and/or orientation. For example, the determined position of the marker block 202 may be compared with a prescribed position of the marker block 202. In such cases, if the determined position of the marker block 202 matches with the prescribed position, the patient 16 is then considered to be correctly positioned. On the other hand, if the determined position of the marker block 202 does not match the prescribed position, the patient 16 is then positioned (e.g., by moving the patient support 14) until the marker block 202 position matches with the prescribed position.

In other embodiments, the determined position and/or orientation of the marker block 202 can be used to determine the position of at least a portion of the patient 16. In such cases, the relative spatial relationship between the marker block 202 and the patient 16 is known or predetermined. As such, once the marker block 202 position is determined, the position of the portion of the patient 16 can then be determined (e.g., via the processing unit 206) based on the relative spatial relationship between the marker block 202 and the patient 16. In some embodiments, by continuously determining the position of the portion of the patient 16 in real time, the portion of the patient 16 can be tracked in real time. The tracked position of the patient 16 may be used to gate an application of radiation provided by the system 10.

In further embodiments, the tracked position of the patient 16 may be used to perform tracking of a target region while an intensity modulated radiation therapy (IMRT) is being performed. In IMRT, a multi-leaf collimator is operated such that a first portion of the target region receives more radiation than a second portion of the target region during a treatment session.

In further embodiments, the determined position of the marker block 202 can be used to determine a level of activity accomplished by the patient 16. For example, if the marker block 202 is placed on the patient's chest, then the determined position of the marker block 202 can be used to determine a level of breathing performed by the patient 16. In some cases, by determining a plurality of positions of the marker block 202 over a period of time, the processing unit 206 can be configured to obtain a plurality of amplitude points that correspond to the patient's levels of breathing at various time points in that period. The determined amplitude points may be used to gate an execution of a procedure, such as, to gate an application of a treatment radiation to the patient 16 for treatment, or to gate an application of an imaging radiation to the patient 16 for imaging purpose. In other embodiments, the determined positions of the marker block 202 (or the amplitude points) may be used to gate a binning of image data, either in real time, or after the image data has been obtained. In further embodiments, the amplitude points may be used to perform tracking of a target region while IMRT is being performed.

Figure 3:
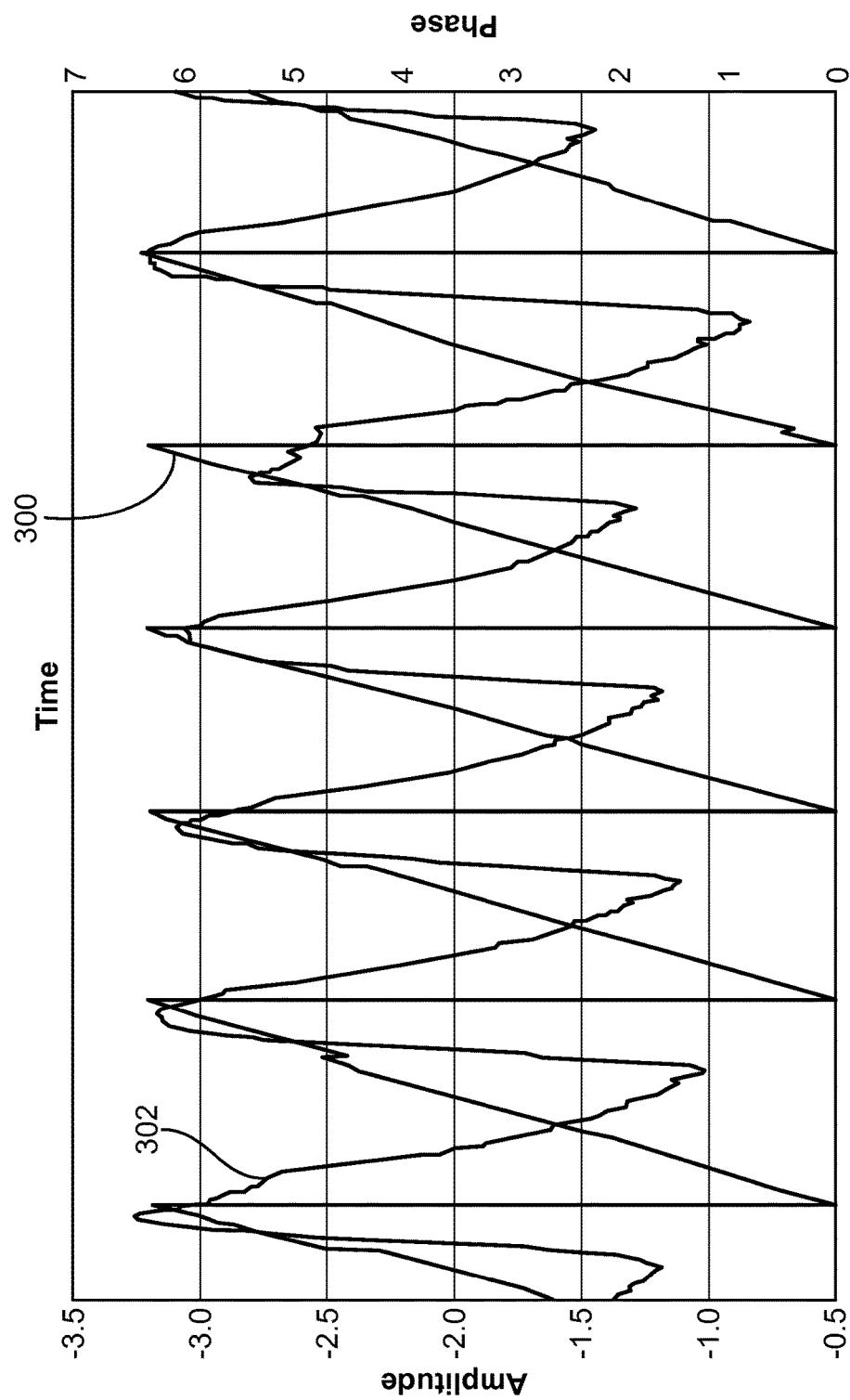
FIG. 3 illustrates an amplitude diagram and a corresponding phase diagram.

In further embodiments, by determining a plurality of positions of the marker block 202 over a period of time, the processing unit 206 can be configured to obtain a plurality of phase points that correspond to different levels of completeness of a breathing cycle at various time points. For example, a phase value may have a value from 0° to 360°, with 0° representing a beginning of a respiratory cycle, and 360° representing an end of the respiratory cycle. FIG. 3 illustrates an example of a phase diagram 300 that is aligned with a corresponding amplitude/position diagram 302. Amplitude diagram 302 includes positional points of the marker block 30 determined using embodiments of the technique described herein. Each point in the amplitude diagram 302 represents a position of the marker block 202 or a bodily part at a certain point in time. In the illustrated example, a phase value of 0° (and 360°) represents a peak of an inhale state, and the phase value varies linearly between 0° and 360° in a physiological cycle. As shown in the diagram, for each point in the amplitude diagram 302 at certain point in time, a corresponding phase value at the same point in time may be obtained. Thus, for each breathing amplitude, the processing unit 206 can determine the corresponding phase of the respiratory cycle.

The determined phase values may be used to gate an execution of a procedure, such as, to gate an application of a treatment radiation to the patient 16 for treatment, or to gate an application of an imaging radiation to the patient 16 for imaging purpose. In further embodiments, the phase values may be used to perform tracking of a target region while IMRT is being performed.

In other embodiments, the determined phase values may be used to gate a binning of image data, either in real time while the image data is being obtained, or after the image data has been obtained. For example, in a 4D-CT imaging session, the marker system 200 may be used to determine the positions of the marker block 202 representing different breathing amplitudes of the patient 16, while a CT machine generates different projection images of the patient 16 at different respective gantry angles. The positions of the marker block 202 may be used to determine breathing phases for association with different projection images. For example, different projection images generated at different gantry angles but belonging to a same phase range (phase bin) may be associated together. The associated projection images may then be used to construct a volumetric CT image for that particular phase bin. Also, in some embodiments, different volumetric CT images for different phase bins may be constructed (e.g., using the processing unit 206 or another processor), and the sequence of volumetric CT images may be displayed in a video.

One advantage to using the marker block 202 is that with a-priori knowledge of the relative positions of the markers 208 on the marker block 202, it is possible to determine all six degrees of freedom (X, Y, Z, $\theta_X$, $\theta_Y$, $\theta_Z$) of the marker block 202 from a single camera view. In other words, only a single camera is required to derive the absolute coordinates of a marker block 202. This results because the relative positioning between the markers 208 on the marker block 202 are known, and the absolute coordinates and viewing orientation of the camera 204 are also known. The detected image of the marker block 202 by the camera 204 indicates the positioning of the visible reference locations 208 relative to the camera's viewing orientation. Because the actual relative positions between the markers 208 are known, the detected relative coordinates of the markers 208 from the camera image can be used to derive the absolute coordinate of the marker block 202. The marker block 202 is also advantageous because its configuration allows the camera 204 to detect the markers 208 accurately.

Although the marker system 200 has been described as having one camera 204, in other embodiments, the marker system 200 can have more than one camera. For example, in alternative embodiments, the marker system 200 may include two cameras which detect the markers 208. In such cases, the processor 54 receives image data from the two cameras, and determines a position of the marker block 202 using triangulation technique, as is known in the art. Also, in other embodiments, instead of a camera, the marker system 200 may include other types of optical devices that are capable of detecting the markers 208.

Figure 4:
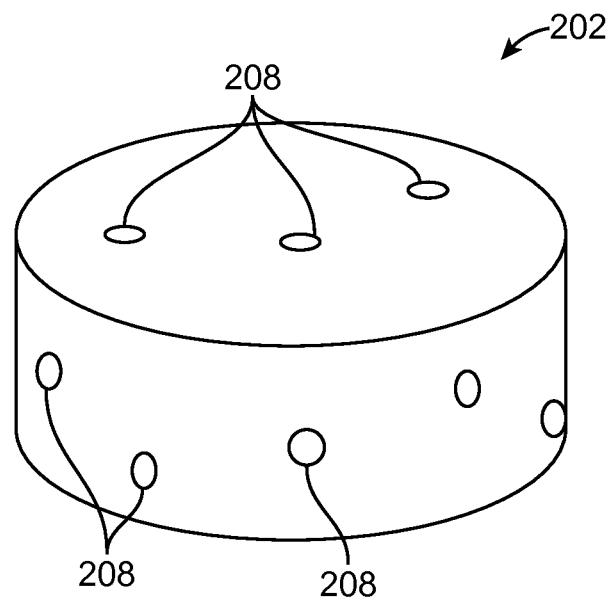
FIG. 4 illustrates a marker block.
Figure 5:
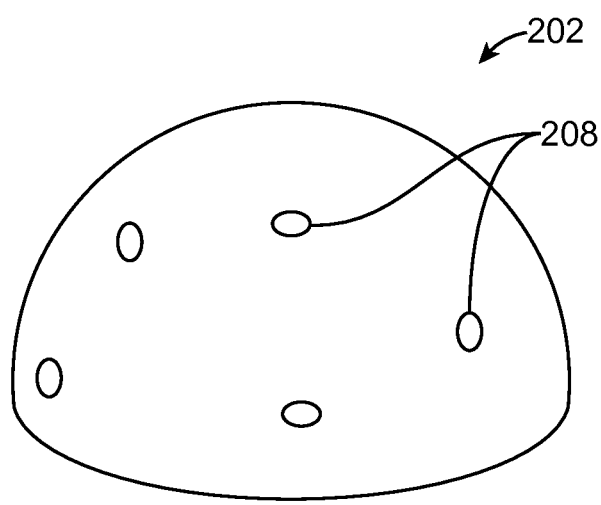
FIG. 5 illustrates another marker block.

In other embodiments, instead of the shape shown in the above example, the marker block 202 can have different shapes. FIG. 4 depicts an embodiment of a marker block 202 having a cylindrical shape with multiple reference locations comprised of markers 208 located on its surface. FIG. 5 depicts an alternate marker block 202 having a hemispherical shape comprised of a plurality of markers 208 attached to its surface.

Figure 6A:
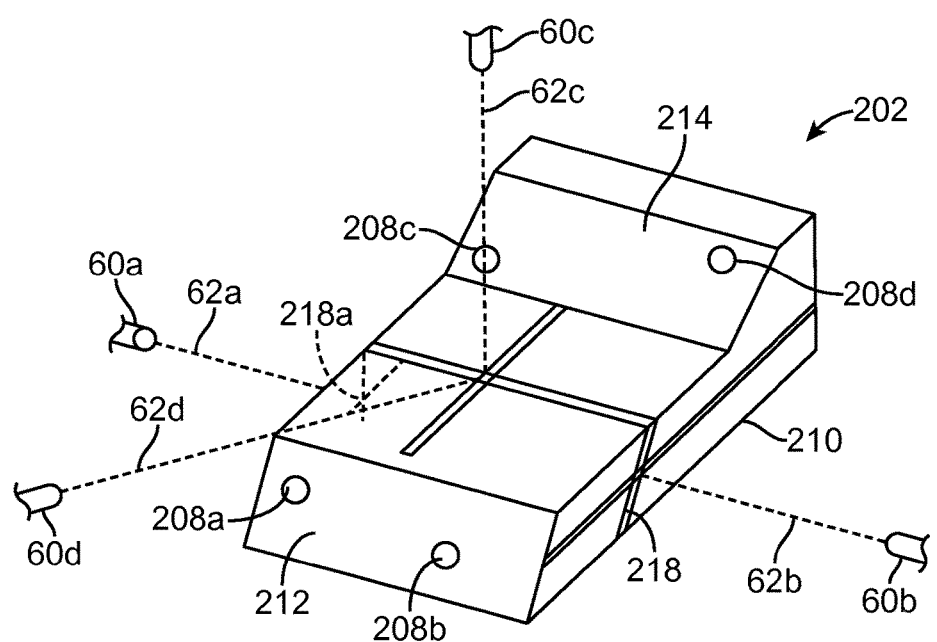
FIG. 6A illustrates another marker block.

In other embodiments, the marker block 202 may have a step configuration. FIG. 6A illustrates another variation of the marker block 202 having a step configuration. The marker block 202 includes a structure 210 having a first surface 212 and a second surface 214, and a plurality of markers 208. The structure 210 can be made from a plastic (e.g., a light weight plastic), or any of other materials. In the illustrated embodiments, the marker block 202 includes four markers 208a-208d, wherein markers 208a, 208b are located on the first surface 212, and markers 208c, 208d are located on the second surface 214. In other embodiments, the marker block 202 may include less than four markers or more than four markers. Also, in other embodiments, the distribution of the markers 208 may be different from that shown in the figure. For example, in other embodiments, the marker 208a may be located on the first surface 212, and markers 208b-208d may be located on the second surface 214.

In some embodiments, each of the markers 208 has a LED with a circular shape. In other embodiments, each LED can have any of other shapes, such as a square, a rectangular, a triangular, an elliptical, or a customized shape. In further embodiments, instead of the LEDs of the markers 208 having the same shape, one or more LEDs of the markers 208 can have a shape that is different from the rest of the LEDs.

In the illustrated embodiments, the marker block 202 also includes markings 218a-218c. The markings 218 may be depressions located on the surface of the marker block 202. Alternatively, the markings 218 may be paint or materials (e.g., polymers) deposited on the surface of the marker block 202. During use, the markings 218 are used to align the marker block 202 with laser beams 62, thereby allowing the marker block 202 to be placed at a prescribed position and orientation. In particular, the marking 218a provides a target associated with laser beam 62a, the marking 218b provides a target associated with laser beam 62b, and marking 218c provides a target associated with laser beams 62c, 62d. In other embodiments, the marking feature may be applied for other embodiments of the marker block 202 described herein, such as the embodiments of the marker block 202 in FIGS. 2, 4, and 5.

Figure 6B:
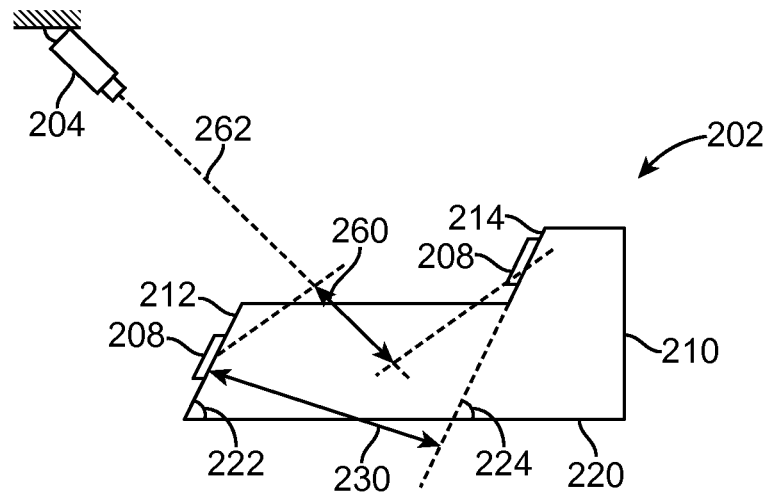
FIG. 6B illustrates another marker block.

FIG. 6B illustrates a side view of the marker block 202 of FIG. 6A in accordance with some embodiments. As shown in the figure, the first and second surfaces 212, 214 of the structure 210 are inclined relative to a base 220 of the structure 210. This provides a larger surface area (as compared to the case when the surfaces 212, 214 are perpendicular to the base 220) of each marker 208 for the camera 204 to detect. In some embodiments, the surfaces 212, 214 may form respective angles 222, 224 with the base 220, wherein each of the angles 222, 224 may be a value that is between 30° and 90°. In other embodiments, the angles 222, 224 may have other values, depending on the position of the camera 204 relative to the marker block 202. For example, the angles 222, 224 may be selected based on the elevation E of the camera 204 relative to the marker block 202, and a horizontal separation H between the camera 204 and the marker block 202 (e.g., angle $222=90°-\tan^{-1}(E/H)$).

As shown in FIG. 6B, the surfaces 212, 214 are parallel to each other. In the embodiments in which the markers 208 have the same shape, such configuration would result in the images of the markers 208 having the same shape as they appear in an image frame generated by the camera 204. Also, as shown in the figure, the surfaces 212, 214 are spaced apart from each other. In some embodiments, the perpendicular spacing 230 between the surfaces 212, 214 may be a value that is at least 0.5 centimeter, and more preferably at least 1.0 centimeter (e.g., 3 centimeters). In other embodiments, the spacing 230 may have different values.

Figure 6C:
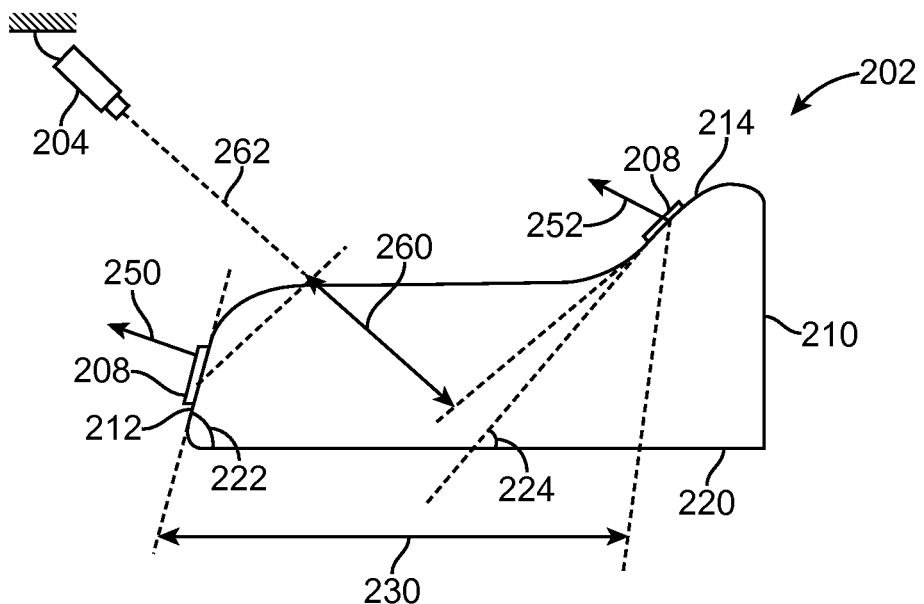
FIG. 6C illustrates another marker block.

In alternative embodiments, the surfaces 212, 214 may not be parallel, and may instead form an angle relative to each other. FIG. 6C illustrates a variation of the marker block 202 in which a first normal 250 of the first surface 212 and a second normal 252 of the second surface 214 form an angle 254. The angle 254 may be a value that is greater than 0° and less than 45°, and more preferably less than 25°. In other embodiments, the angle 254 can have other values. As shown in the figure, the first and second surfaces 212, 214 are spaced by a distance 230.

In some embodiments, the camera 204 is so positioned relative to the marker block 202 such that a spacing 260 between the first and second surfaces 212, 214 (and therefore, between a marker 208 on the first surface 212 and another marker 208 on the second surface 214) measured in the viewing direction 262 of the camera 204 is a value that is at least 0.5 centimeter, and more preferably at least 1.0 centimeter (e.g., 3 centimeters). In some cases, the value of the spacing 260 may be the same as the value of the spacing 230. In other cases, the value of the spacing 260 may be different from the value of the spacing 230.

Figure 6D:
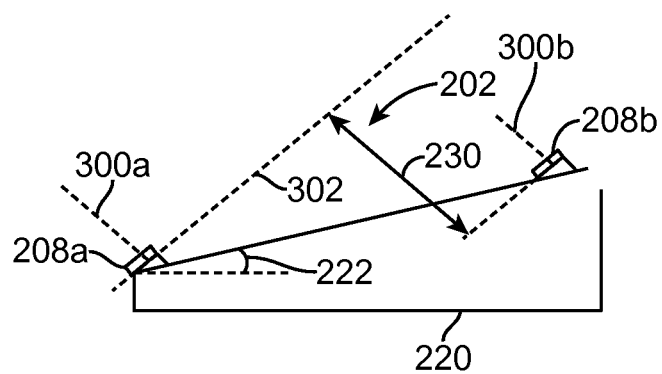
FIG. 6D illustrates another marker block.

FIG. 6D illustrates a variation of the marker block 202 in accordance with other embodiments. In the illustrated embodiments, the marker block 202 has a surface 212, and the markers 208a, 208b are located on the surface 212. The marker 208a has a normal 300a, and the marker 208b has a normal 300b. In some embodiments, each normal 300 is a vector that points towards a direction from which the marker 208 is intended to be viewed. Alternatively, each normal 300 may be defined as a vector that points towards a direction, onto which a projected area of the marker 208 is maximized. As shown in the figure, the normals 300a, 300b are parallel to each other. Alternatively, the normals 300a, 300b may form an angle that is less than 45°, and more preferably less than 25°.

In the illustrated embodiments, the marker 208b is spaced at a distance 230 from a plane 302 that intersects the marker 208a and that is perpendicular to the normal 300a. In such configuration, the markers 208a, 208b are spaced from each other. In some embodiments, the distance 230 is at least 0.5 centimeter, and more preferably at least 1.0 centimeter. Also as shown in the figure, the surface 212 forms an angle 222 with a base 220. In some embodiments, the angle 222 is selected such that the markers 208a, 208b are oriented approximately towards the camera 204. In other embodiments, the angle 222 may be predetermined without regards to the location of the camera 204. In such cases, when using the marker block 202, the camera 204 is positioned such that the markers 208a, 208b face approximately towards the camera 204. In some embodiments, the camera 204 is positioned relative to the marker block 202 such that a distance between the markers 208a, 208b measured in a viewing direction of the camera 204 is at least 0.5 centimeter, and more preferably at least 1.0 centimeter.

The marker block 202 with markers 208 on multiple steps (like those shown in FIGS. 6A-6D) is advantageous because changes in rotation of the marker block 202 can be more easily detected by the single camera 204 than markers on a single rectilinear plane. For any rotation of the marker block 202 (except about the camera axis), the markers 208 in the plane (e.g., plane 212) closer to the camera 204 will move over a larger angle as seen by the camera 204 than the markers 208 in the plane (e.g., plane 214) farther away from the camera 204. Therefore, the tracking system can be much more sensitive to changes in rotation than with a single-plane marker block, in which all the markers will move approximately over the same angle for a given rotation. By placing markers 208 in a step configuration, the normals of the markers 208 themselves can point approximately towards a same direction (e.g., towards the camera 204), while still being at different depths away from the camera 204. In some embodiments, two markers 208 are considered as facing approximately a same direction when the respective directions in which the two respective markers 208 face do not vary by more than 30°, and more preferably, do not vary by more than 15°.

Figure 7:
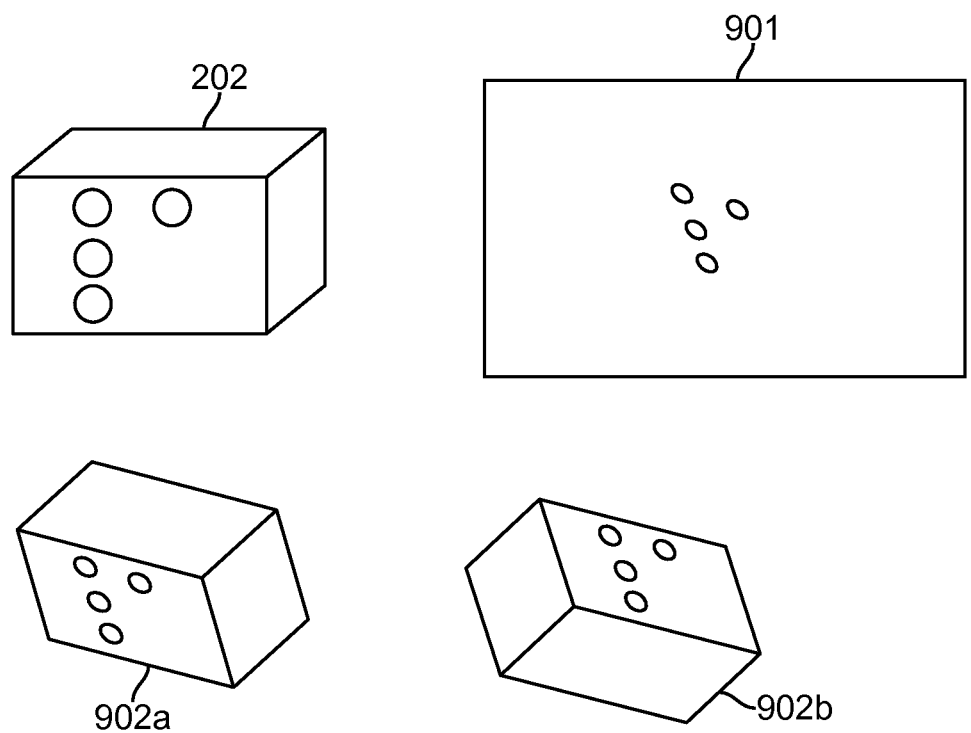
FIG. 7 illustrates an image analysis concept.

Furthermore, the marker block 202 with markers 208 on multiple steps avoids a certain ambiguity that is present for marker blocks with all markers on one rectilinear plane. FIG. 7 illustrates such principle. Given a marker block 202, the camera 204 will form an image 901 of the markers as seen by the camera 204. Note that given the image 901, the orientation of the block 202 could be interpreted two different ways 902a, 902b. Thus the available image 901 results in an ambiguity in the position of the marker block 202. The multiple plane maker block 202 avoids this ambiguity because the relationship between the two planes in the image will be different depending on the orientation of the structure 210. Therefore the ambiguity illustrated in the example of FIG. 7 is avoided.

In other embodiments, the marker block 202 can be formed with shapes to fit particular body parts. For example, molds or casts that match to specific locations on the body can be employed as marker blocks 202. Marker blocks 202 shaped to fit certain areas of the body facilitate the repeatable placement of the marker blocks 202 at particular locations on the patient. Alternatively, the marker blocks 202 can be formed to fit certain fixtures that are attached to a patient's body. For example, a marker block 202 can be formed within indentations and grooves that allow it to be attached to eyeglasses, to a patient's clothing, or to a patient's skin. In yet another embodiment, the fixtures are formed with integral marker block(s) 202 having markers 208 on them.

In further embodiments, instead of the structure 210 being a non-human object, the structure 210 may be a portion of the patient 16. In such cases, the first surface 212 would be a first portion of the patient 16, the second surface 214 would be a second portion of the patient 16, and the markers 208 are then individually secured to, or placed on, the portions of the patient 16. In some embodiments, each marker 208 may include a LED secured to a base, wherein the base has an adhesive for attachment to the patient 16 or to a patient's clothing. In some cases, the adhesive may be made from a biocompatible material to reduce a risk of a skin irritation.

Also, it should be understood by those skilled in the art that the marker system 200 can be used with different systems in different embodiments. For example, the radiation system 10 needs not be a treatment device, and may be any machine that is capable of generating a radiation beam. In some embodiments, the radiation system 10 may be any types of imaging or optical devices, such as a CT imaging device (e.g., a cone beam CT device), a laminar tomography machine, a MRI machine, a C-arm based x-ray imaging machine, a three dimensional angiography machine, or a PET machine. Also, in other embodiments, any of the marker systems 200 and/or methods described herein can be used with non-imaging devices, such as a positioner or a treatment machine that has no imaging capability. In further embodiments, any of the marker systems 200 and/or methods described herein can be used with a machine that has a plurality of radiation sources. For example, the machine can have a first radiation source for delivering diagnostic radiation (e.g., radiation having an energy level in the kilo-electron-volt range), and a second radiation source for delivering treatment radiation (e.g., radiation having an energy level in the mega-electron-volt range). As another example, the machine can also have a plurality of diagnostic radiation sources and/or one or more treatment radiation sources.

Figure 8A:
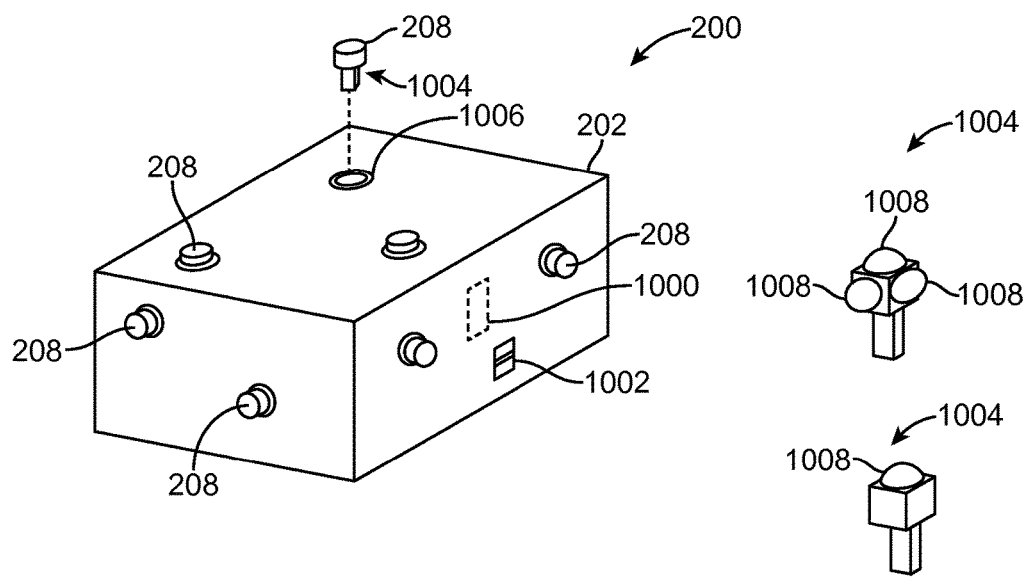
FIG. 8A illustrates a marker system.

In the above embodiments, the marker block 202 has been described as having multiple markers 208 that emit light. In some embodiments, the markers 208 include respective LED units 1004 that may receive power from a battery 1000 in the marker block 202 (FIG. 8A). Each LED unit 1004 may be permanently secured to the marker block 202. Alternatively, each LED unit 1004 may be a LED bulb that is detachably secured to the marker block 202. For example, the marker block 202 may include a plurality of LED bulb sockets for receiving respective LED units 1004 (e.g., LED bulbs). This way, a LED unit 1004 may be replaced if necessary. The marker block 202 may also include a switch 1002 for switching on all of the LED markers 208. Alternatively, the marker block 202 may have a plurality of switches or a user interface that allows certain one(s) of the markers 208 be switched on. As shown in the figure, the marker block 202 may also include a plurality of sockets 1006 for receiving the respective LED units 1004. Each socket 1006 is configured to provide current to drive a respective LED unit 1004. In some embodiments, a LED unit 1004 may include one LED 1008. In other embodiments, a LED unit 1004 may include multiple LEDs 1008. Also, in other embodiments, instead of using the battery 1000, the marker system 200 may include a power cable for coupling to an electrical outlet at a wall, wherein the power cable supplies power to drive the LED units 1004. In addition, in some embodiments, the marker block 202 may include markings 218, like those described with reference to FIG. 6A.

Figure 8B:
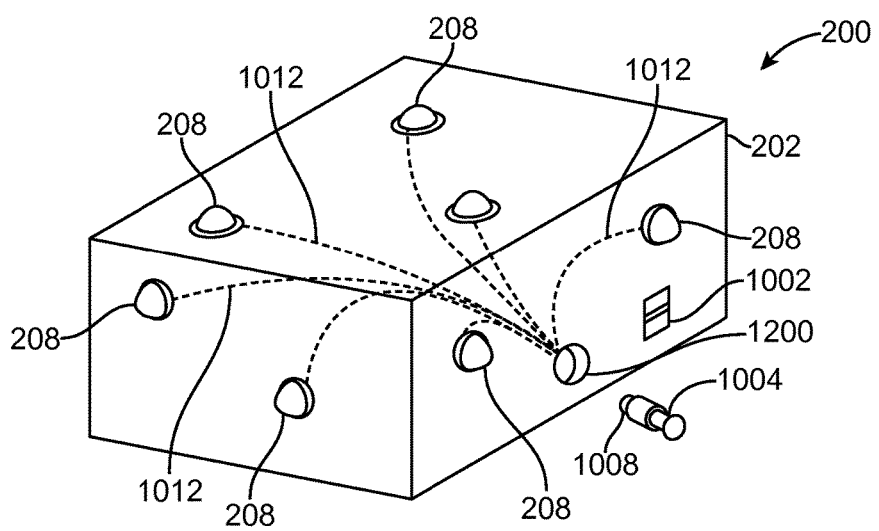
FIG. 8B illustrates another marker system.

In other embodiments, instead of having multiple LED units 1004 for the respective markers 208, two or more of the markers 208 may share the same LED unit 1004. In such cases, the marker block 202 may include a LED unit 1004 therein that provides light for two or more (e.g., all) of the markers 208 through fiber optics (or optical fibers) 1012 (FIG. 8B). As shown in the figure, the marker block 202 may include an opening 1200 for allowing the LED unit 1004 to insert therein, and be secured to a socket (not shown) in the marker block 202. The LED unit 1004 may include one LED 1008 or a plurality of LEDs 1008. When the LED unit 1004 is inserted into the marker block 202, light from the LED unit 1004 is transmitted by fiber optics 1012 to respective markers 208. In some embodiments, the LED unit 1004 may be permanently secured to the marker block 202. Alternatively, the LED unit 1004 may be a LED bulb that is detachably secured to the marker block 202. This way, the LED unit 1004 may be replaced if necessary. In the illustrated embodiments, each marker 208 may include a transparent window for allowing light transmitted by the fiber optic 1012 to exit therethrough. In some embodiments, the transparent window may be implemented as an end of an optical fiber, or a lens. The ends of the fiber optics are located next to the transparent windows of the respective markers 208, and emit light through the transparent windows. The LED unit 1004 may be driven by a battery located in the marker block 202. Alternatively, the marker system 200 may include a power cable for coupling to an electrical outlet at a wall, wherein the power cable supplies power to drive the LED unit 1004. In addition, in some embodiments, the marker block 202 may include markings 218, like those described with reference to FIG. 6A.

Figure 8C:
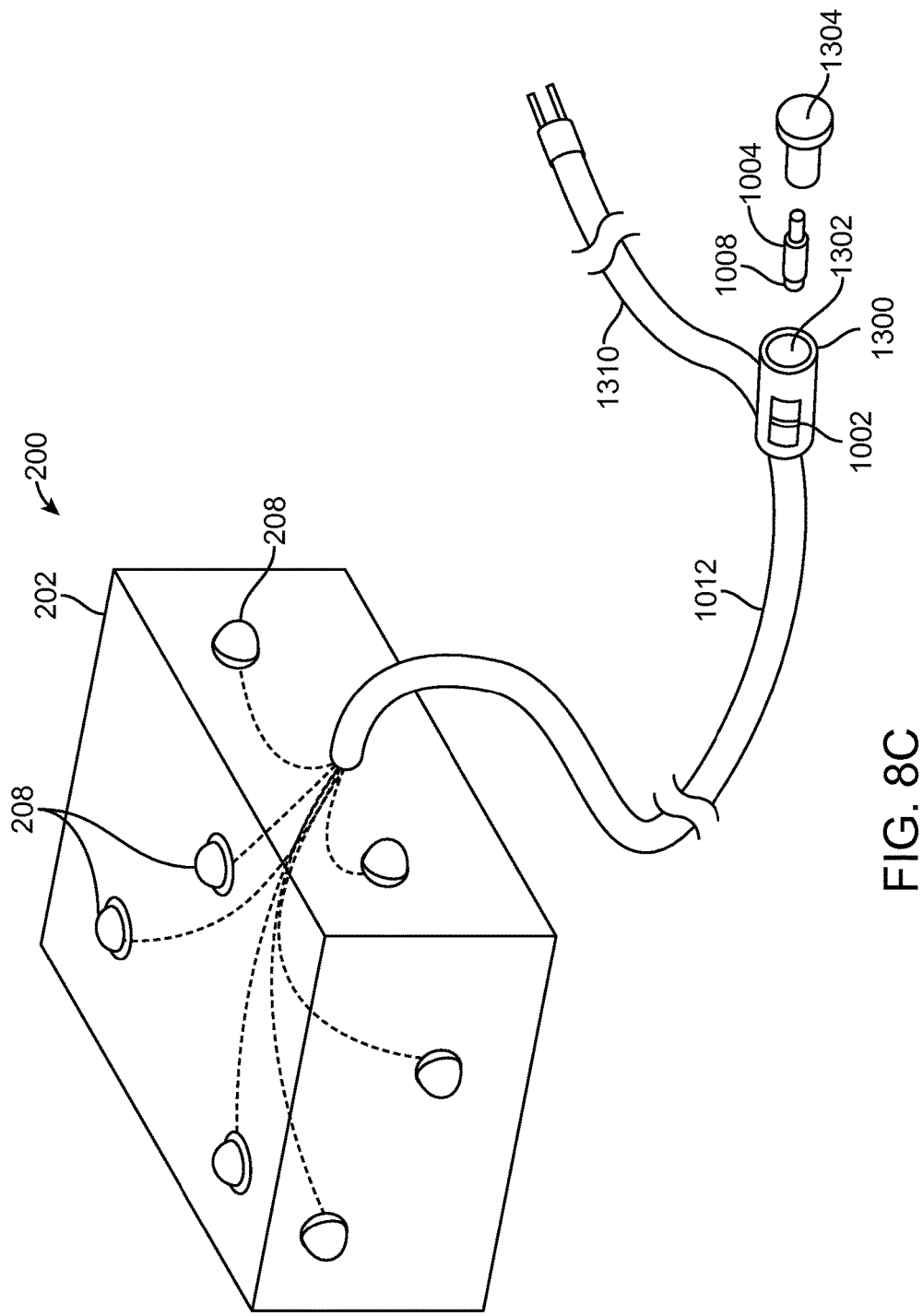
FIG. 8C illustrates another marker system.

In further embodiments, the fiber optics 1012 may extend out of the marker block 202 to couple to a LED unit 1004 that is remote from the marker block 202 (FIG. 8C). The LED unit 1004 may include one LED 1008 or a plurality of LEDs 1008. In such cases, each marker 208 may include a transparent window for allowing light transmitted by the fiber optic 1012 to exit therethrough. In some embodiments, the transparent window may be implemented as an end of an optical fiber, or a lens. Such configuration may be advantageous because it eliminates all circuits in the marker block 202, and the entire marker block 202 with the markers 208 may be made from non-metallic material. Accordingly, the marker block 202 may be used in an imaging procedure (e.g., x-ray, CT scan, etc.) without causing metal artifacts in images. As shown in the figure, the marker system 200 also includes a socket 1300 coupled to the end of the fiber optics 1012. The socket 1300 includes a cavity 1302 for detachably receiving the LED unit 1004 (e.g., a LED bulb), and a closure unit 1304 for closing the socket 1300. In some embodiments, the LED unit 1004 may be detachably inserted into a cavity of the closure unit 1034, and is then inserted into the cavity 1302 of the socket 1300. The socket 1300 also includes a switch 1002 for turning the LED unit 1004 on or off. The marker system 200 also includes a power cable 1310 for coupling to an electrical outlet at a wall. Alternatively, instead of the power cable 1310, the marker block 202 may include a battery cavity for receiving a battery to drive the LED unit 1004. In addition, in some embodiments, the marker block 202 may include markings 218, like those described with reference to FIG. 6A.

Figure 8D:
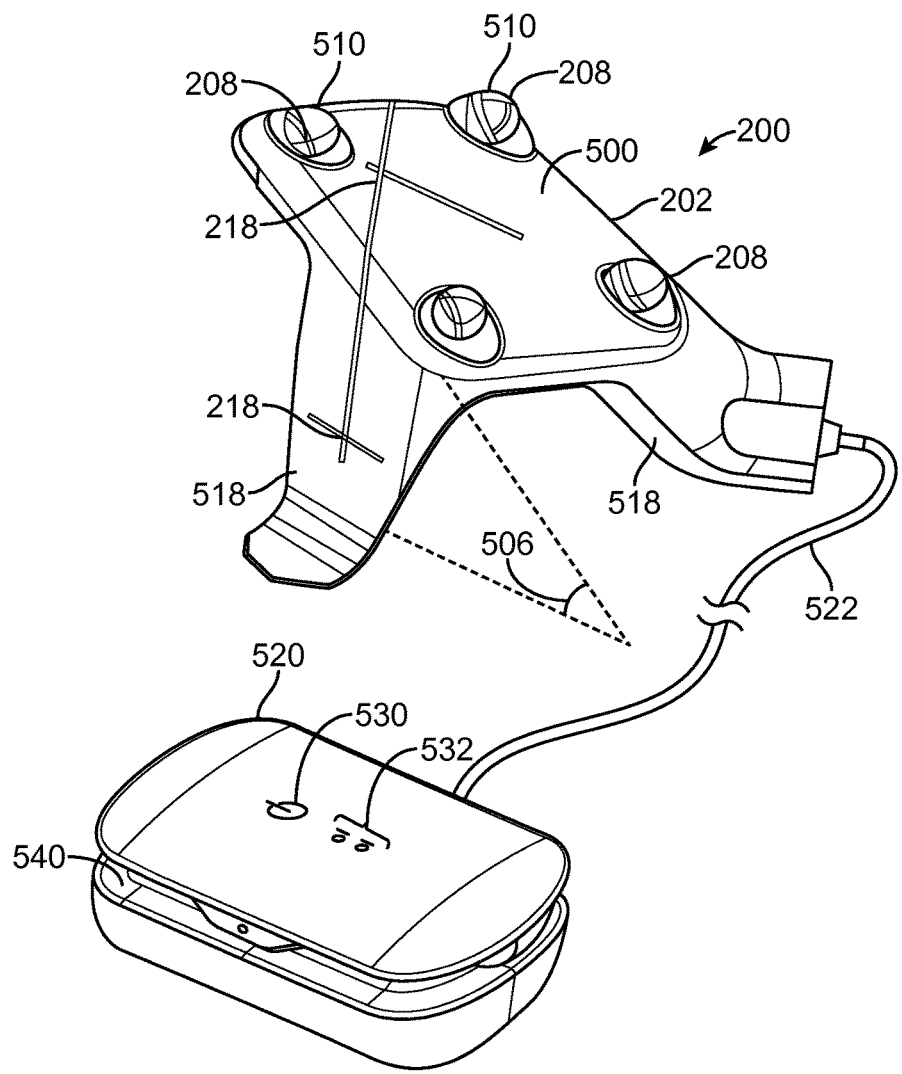
FIGS. 8D-8E illustrate another marker system.
Figure 8E:
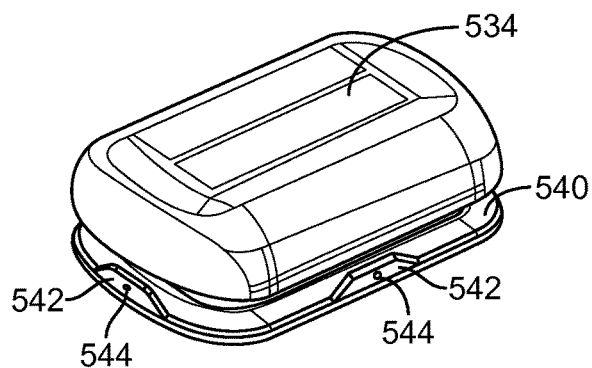

FIGS. 8D-8E illustrate another marker system 200 in accordance with other embodiments. The marker system 200 includes a marker block 202 with a plurality of markers 208. The marker system 200 is similar to the embodiments discussed with reference to FIGS. 2 and 4-6, except that the shape of the marker block 202 is different. The marker block 202 has a surface 500 tilted to form an acute angle 506 relative to a horizontal line or a surface on which the marker block 202 is supported. In the illustrated embodiments, the markers 208 comprise respective LEDs that are fitted underneath clear acrylic domes 510 to protect them while still allowing a spread of light over an azimuthal spread of 90° (e.g., ±45°) or more (e.g., an azimuthal spread of ±90°), so that the marker block 202 is detectable by the camera 204 over at least a ±45° lateral rotation, and more preferably, at least a ±90° lateral rotation. In some embodiments, the marker block 202 allows the markers 208 to be accurately detected even if the patient support is rotated about a vertical axis by up to 90° (which corresponds to rotating the marker block 202 about a vertical axis by up to 90°).

In some embodiments, each LED is configured to emit infrared light. In other embodiments, each LED is configured to emit visible light. In further embodiments, each LED may be configured to emit ultraviolet (UV) light.

As shown in the figure, the marker block 202 has a thin configuration, and the planar structure (with the top surface 500) supporting the LEDs is raised and supported by three support structures 518. Such configuration provides a marker block 202 that is lightweight, and allows the LEDs to be mounted at desired elevations. In other embodiments, the marker block 202 may have a planar bottom structure to which the LEDs are secured. In such cases, the marker block 202 may further include light-pipes (e.g., fiber optics) for transmitting light from the LEDs to the marker windows 510 at the top structure that is above the bottom structure. In one implementation, the light-pipes may be straight vertical light-pipes. In further embodiments, the light-pipes may have bends (e.g., 90° bends) to direct and/or spread the light out in a certain direction.

In the illustrated embodiments, the marker block 202 also includes markings 218 (which may be similar to those described with reference to FIG. 6A). The markings 218 may be depressions located on the surface of the marker block 202. Alternatively, the markings 218 may be paint or materials (e.g., polymers) deposited on the surface of the marker block 202. During use, the markings 218 are used to align the marker block 202 with laser beams, thereby allowing the marker block 202 to be placed at a prescribed position and orientation.

In the illustrated embodiments, the marker block 202 is attached to an electronic module 520 via a cable 522 (e.g., a lightweight tether). The module 520 is configured to provide a user interface for allowing a user to control the marker block 202. The module 520 has a power switch 530, which when activated, provides a constant current to power the LEDs for the respective markers 208. The module 520 also has one or more indicators 532 for indicating low battery and/or fault condition. In the illustrated embodiments, the module 520 includes rechargeable batteries (or battery) that are contained in a housing of the module 520, and are covered by a battery door 534 (FIG. 8E). In other embodiments, the batteries (or battery) may be non-rechargeable. Also, in further embodiments, the module 520 may not include any battery. Instead, the module 520 may include a power cable configured for detachably coupling to an electrical outlet at a wall. In addition, in other embodiments, the module 520 may not include the switch 530. Instead, the LEDs will emit light as soon as batteries or battery is installed. Having the electronics separated from the marker block 202, and placing them into the module 520 are advantageous because such configuration allows the marker block 202 to be as radio-transparent as possible. As a result, the marker block 202 may be used in a high radiation environment (e.g., with a radiation treatment machine) with minimal damage or interference with the radiation.

In further embodiments, both the marker block 202 and the module 520 may have respective battery compartments for accommodating their own batteries. In such cases, the marker block 202 may be selectively used with or without the module 520. Without the electronic module 520, the user has the advantage of not having to deal with coupling the marker block 202 with the module 520. With the electronic module 520, the user has the advantage of a longer operational time since the battery in the module 520 may be bigger and may last longer.

The cable 522 may be wrapped around the side of the module 520, which includes a channel 540 for accommodating the cable 522. Such feature permits easy carrying of the module 520 in one hand. The module 520 also includes a plurality of tabs 542 (e.g., strain relief tabs) at the perimeter for containing and protecting the wrapped cable 522. Each tab 542 has an opening for gripping the cable 522 (e.g., end of the cable 522). In some embodiments, one end of the cable 522 may be detachably coupling to the marker block 202. In other embodiments, one end of the cable 522 may be detachably coupling to the module 520. In further embodiments, opposite ends of the cable 522 may be detachably coupling to the marker block 202 and to the module 520, respectively. Detachably coupling the end of the cable 522 to one or both of the marker block 202 and the module 520 allows the marker block 202 and the module 520 to be serviced separately if needed. In other embodiments, the cable 522 may be fixedly secured to both the marker block 202 and the module 520 so that the cable 522 is not detachable from the marker block 202 and the module 520. In further embodiments, the module 520 may include a spring mechanism for automatically retracting the cable 522 into the channel 540 of the module 520. For example, in one implementation, the spring mechanism may be configured to automatically wind the cable 522 to thereby retract the cable 522.

In further embodiments, the module 520 may be coupled to the marker block 202 so that the assembly is easy to carry in one hand. For example, in some embodiments, the module 520 may be detachably coupled to a surface on the opposite side of the surface 500 (e.g., using a hook-and-loop connector, a snap-fit connector, a slide-in-groove connector, etc.). Such configuration allows the module 520 to be nested partially inside the marker block 202. In other embodiments, the marker block 202 may be nested at least partially inside the module 520.

In still further embodiments, the marker system 200 may not include the module. Instead, all electronics and batteries for the system 200 are enclosed within the marker block 202 itself. To minimize interference with operation of a radiation device, ultra-thin batteries may be used. For example, Thinergy battery from infinite Power Solutions may be used. In other embodiments, to further minimize interference with operation of a radiation device, the marker block 202 may not include any battery. Instead, the marker block 202 may include a power cable for detachably coupling to electrical outlet at a wall for receiving power.

In other embodiments, the marker block 202 of FIGS. 8A-8E may have other configurations, such as the any of the shapes shown in FIGS. 4-6D.

Figure 9A:
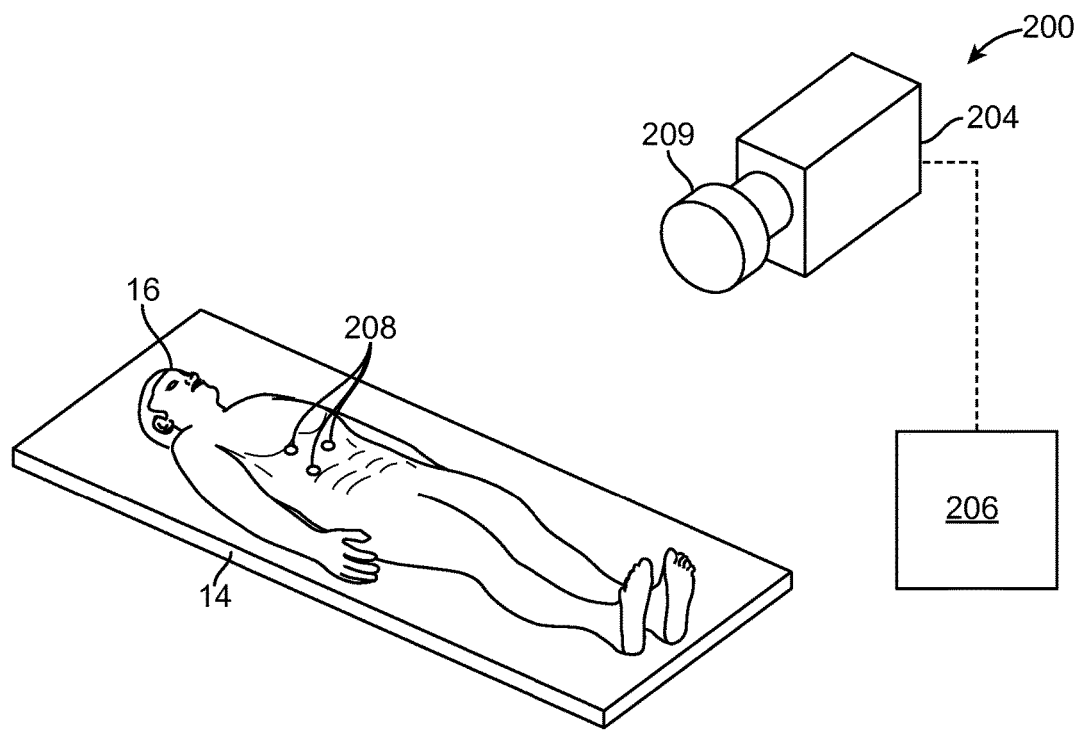
FIG. 9A illustrates another marker system.
Figure 9B:
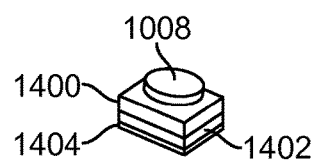
FIG. 9B illustrates a marker.
Figure 9C:
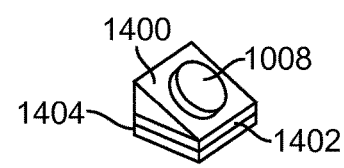
FIG. 9C illustrates another marker.

In the above embodiments, the marker system 200 has been described as having a marker block 202. In other embodiments, the marker block 202 may not be included. For example, in other embodiments, the marker system 200 may include a plurality of markers 208 that can be individually detachably coupled to the patient 16 (FIG. 9A). Each marker 208 may include a LED (or a plurality of LEDs) 1008 coupled to a base 1400, an adhesive 1402 at the bottom of the base 1400, and a cover 1404 covering the adhesive 1402 (FIG. 9B). During use, the cover 1404 may be removed to expose the adhesive 1402, and the base 1400 may be coupled to the patient 16 using the adhesive 1402. For example, the base 1400 may be coupled to the patient 16 by directly securing the base 1400 to the patient 16. Alternatively, the base 1400 may be coupled to the patient 16 indirectly by securing the base to a patient's clothing, eye glasses, etc. In some embodiments, the adhesive 1402 may be made from a biocompatible material to reduce or minimize the risk of a skin reaction. In other embodiments, instead of the adhesive 1402, the marker 208 may include other types of securing mechanism, such as a clamp, a clip, a pin, etc. Also, in some embodiments, the LED 1008 may be permanently secured to the base 1400. In other embodiments, the LED 1008 may be a part of a LED unit (e.g., a LED bulb) that is detachably coupled to the base 1400, so that the LED unit (e.g., LED bulb) may be replaced if necessary. In addition, in other embodiments, instead of having the shape shown in FIG. 9B, the base 1400 may have a tilted configuration for oriented the LED(s) 1008 at a certain angle (FIG. 9C). In further embodiments, the base 1400 may have a base portion and an upper portion that is coupled and rotatable relative to the base portion, wherein the LED(s) 1008 may be coupled to the upper portion. Such configuration allows the angle or orientation of the LED(s) 1008 be adjusted by rotating the upper portion relative to the base portion.

Figure 9D:
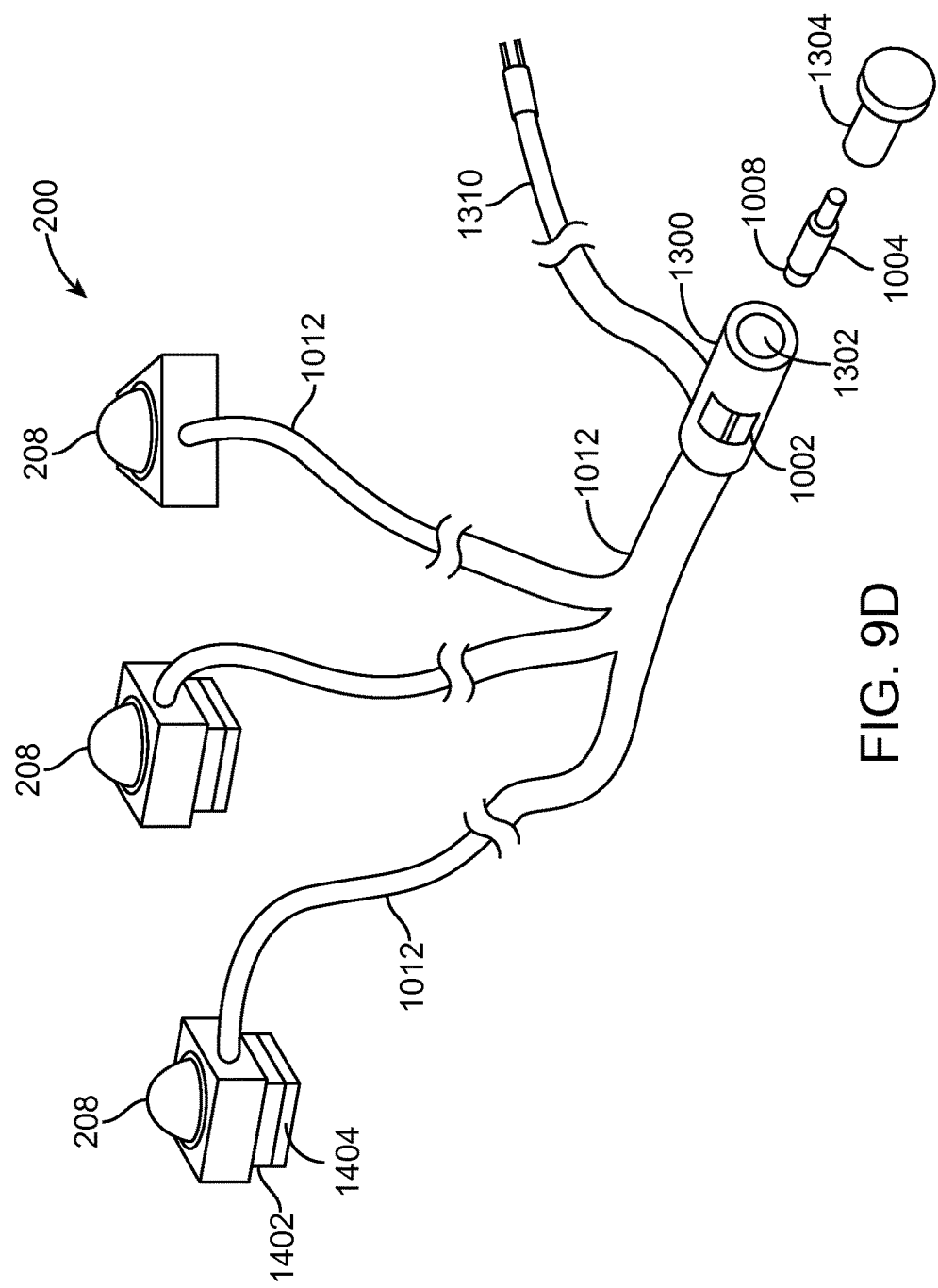
FIG. 9D illustrates another marker system.

In further embodiments, the plurality of markers 208 may use the same LED unit. For example, in some embodiments, the plurality of markers 208 may have respective optical fiber 1012 coupled thereto, wherein the optical fibers 1012 are configured to transmit light from a LED unit 1004 (FIG. 9D). In such cases, each marker 208 has a transparent window for allowing light transmitted by the optical fiber 1012 to exit therethrough. The optical fibers 1012 converge into an optical fiber cable at the other end. In some cases, the transparent window may be implemented as an end of an optical fiber, or a lens. Such configuration may be advantageous because it eliminates all circuits in the markers 208, and the entire marker 208 may be made from non-metallic material. Accordingly, the markers 208 may be used in an imaging procedure (e.g., x-ray, CT scan, etc.) without causing metal artifacts in images. As shown in the figure, the marker system 200 also includes a socket 1300 coupled to the end of the fiber optics 1012. The socket 1300 includes a cavity 1302 for detachably receiving the LED unit 1004 (e.g., a LED bulb), and a closure unit 1304 for closing the socket 1300. In some embodiments, the LED unit 1004 may be detachably inserted into a cavity of the closure unit 1034, and is then inserted into the cavity 1302 of the socket 1300. The socket 1300 also includes a switch 1002 for turning the LED unit 1004 on or off. The marker system 200 also includes a power cable 1310 for coupling to an electrical outlet at a wall. Alternatively, instead of the power cable 1310, the marker system 200 may include a battery cavity for receiving a battery to drive the LED unit 1004.

In the above embodiments of FIGS. 2, 4-6, 8, and 9, the marker system 200 has been described as having one or more LEDs as light sources for providing light for emission out of the markers 208. In other embodiments, instead of LEDs the light sources may be other types of light bulbs, such as halogen light bulbs, CFL bulbs, incandescent bulbs, etc.

Also, in one or more of the embodiments of FIGS. 2, 4-6, 8, and 9, the marker system 200 may include electronics for communicating (e.g., wirelessly) with another device or with a user. Such feature may allow the system 200 to respond intelligently to a status of a treatment and/or gating conditions. For example, in some embodiments, the marker block 202 may include a wireless transmitter for providing information (such as, a signal indicating that the marker block 202 is "locked" to a tracking system) to a user. In other embodiments, instead of a transceiver, the marker block 202 may include a visible indicator (e.g., a visible LED on the marker block 202) for indicating certain information to the user. In further embodiments, the marker system 200 may be configured to communicate with a medical device, such as a radiation treatment device. For example, the marker system 200 may include a transmitter for sending a signal to stop the radiation treatment device when certain conditions are detected (e.g., when the camera 204 cannot detect a sufficient number of markers, etc.). The marker system 200 may also include other types of communication devices in other embodiments. For example, in other embodiments, the marker system 200 may be configured to flash warning lights, display status messages (e.g., on a display), and/or transmit audio signal(s).

Furthermore, in one or more of the embodiments of FIGS. 2, 4-6, 8, and 9, the marker system 200 may optionally further include a microphone. For example, in the marker system 200 that includes the marker block 202, the microphone may be placed at the marker block 202.

In addition, in one or more of the embodiments of FIGS. 2, 4-6, 8, and 9, the marker system 200 may be configured to modulate light output to reject background light and/or to get position information by phase sensitive detection.

In further embodiments, the marker system 200 may use one or more light sources that do not require a battery or power from an electrical outlet, and that do not use any reflector to reflect light for detection by the camera 204. For example, in some embodiments, each marker 208 may include a phosphorescent dye or material with a long afterglow lasting on the order of several minutes to several hours. In such cases, the material may be excited by irradiating it with light at an absorbing wavelength for a relatively long duration (e.g., on the order of several minutes to several hours). The light irradiation (for "charging" the marker material) may occur in a dedicated assembly/station that is not a part of the treatment system, and which may be located inside or outside of the treatment room. After the light irradiation is completed, the marker system 200 is then ready for use (e.g., in a treatment procedure). During a treatment procedure, the camera 204 detects light emitted from the phosphorescent markers 208. In such configuration, because the markers 208 themselves emit light, the system 200 does not require a light source to emit light from the direction of the camera 204, and the system 200 does not use any reflected light from the markers 208.

In another example, each marker 208 may include a fluorescent dye or other fluorescent material that absorbs light at one wavelength (e.g., a first center wavelength) and emits light at a different wavelength (e.g., a second center wavelength) in response to absorbing the light at the first wavelength. In one implementation, the camera 204 may include a ring illuminator that direct light at the absorbing wavelength of the fluorescent material, and a bandpass filter whose passband is at the emitting wavelength of the fluorescent material. Thus, the camera 204 does not detect any reflection of the illuminating light (provided from the ring illuminator), and only detects the light emitted from the fluorescent markers 208. An example of fluorescent material that may be used is the TL-0156 fluorophore from Tailorlux, which absorbs light at 450 nm, and emits light at 735 nm.

Thus, as used in this specification, the term "light source" may refer to any source that provides light without using a reflector that reflects light provided from an external illuminator aimed towards the reflector. For example, the term "light source" may refer to a source that generates light using power received from a power source, such as a battery or an electrical outlet. As another example, the term "light source" may refer to a source having a material that emits light in response to the material absorbing energy (such as light from another source, heat, etc.).

Also, in other embodiments, instead of using markers that emit light and camera that detects light, other types of energy/signal emitting devices and signal detectors may be used. For example, in other embodiments, electromagnetic field beacons may be used as markers that emit electromagnetic signals. In one implementation, Calypso beacons available from Varian Medical Systems, Inc. may be placed on a marker block. The beacons provide electromagnetic emission and the positions of the beacons may be detected by an electromagnetic detector array that is exterior to the patient. In some embodiments, the beacons may be excited by an external source. In further embodiments, instead of light or electromagnetic signal, the markers may emit other types of signal.

Computer System Architecture

Figure 10:
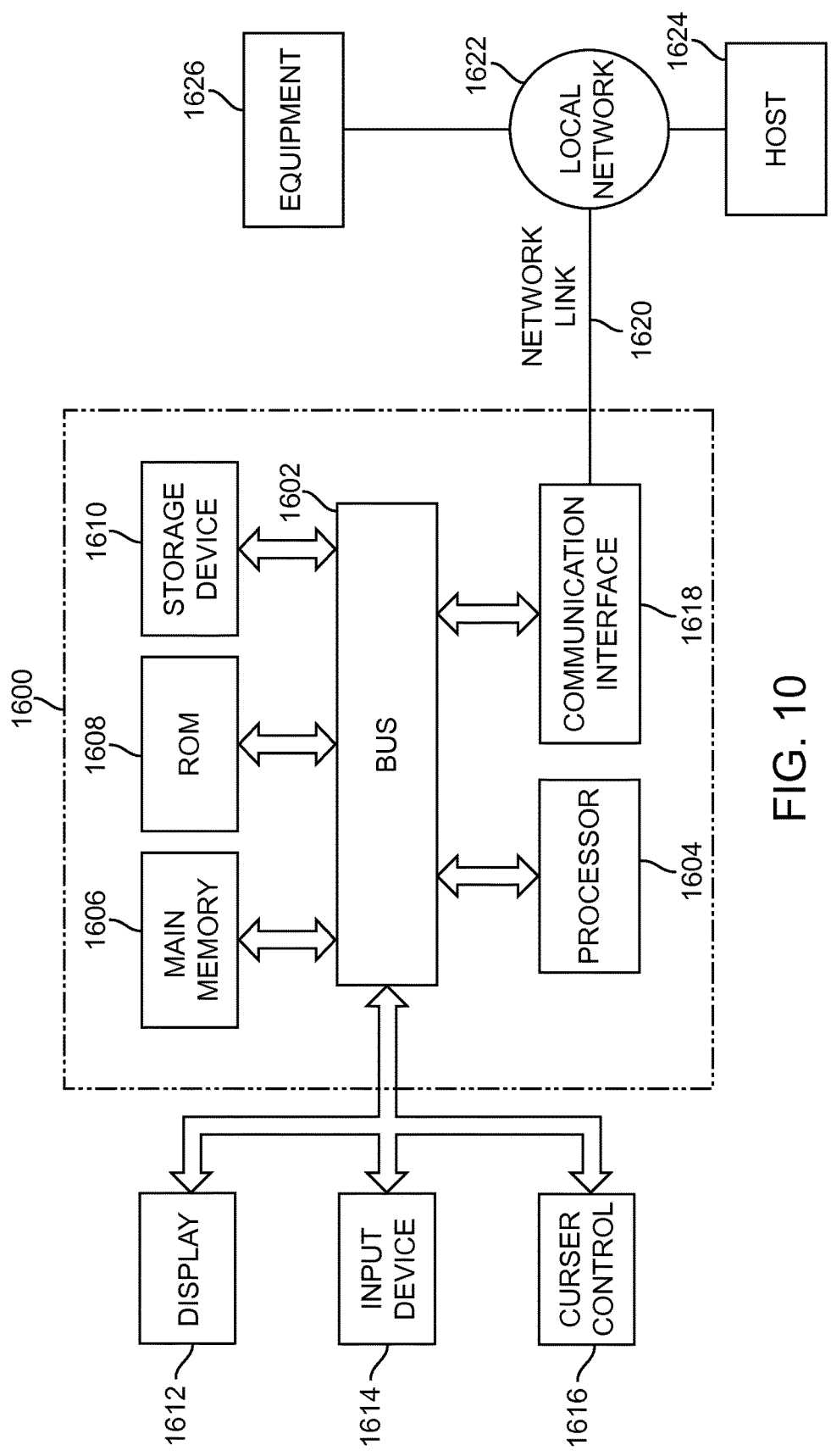
FIG. 10 illustrates a computer system.

FIG. 10 is a block diagram illustrating an embodiment of a computer system 1600 that can be used to implement various embodiments described herein. Computer system 1600 includes a bus 1602 or other communication mechanism for communicating information, and a processor 1604 coupled with the bus 1602 for processing information. The processor 1604 may be an example of the processor 54 of FIG. 1, an example of the processing unit 206 of FIG. 2, or an example of any processor described herein. The computer system 1600 also includes a main memory 1606, such as a random access memory (RAM) or other dynamic storage device, coupled to the bus 1602 for storing information and instructions to be executed by the processor 1604. The main memory 1606 also may be used for storing temporary variables or other intermediate information during execution of instructions to be executed by the processor 1604. The computer system 1600 further includes a read only memory (ROM) 1608 or other static storage device coupled to the bus 1602 for storing static information and instructions for the processor 1604. A data storage device 1610, such as a magnetic disk or optical disk, is provided and coupled to the bus 1602 for storing information and instructions.

The computer system 1600 may be coupled via the bus 1602 to a display 167, such as a cathode ray tube (CRT), for displaying information to a user. An input device 1614, including alphanumeric and other keys, is coupled to the bus 1602 for communicating information and command selections to processor 1604. Another type of user input device is cursor control 1616, such as a mouse, a trackball, or cursor direction keys for communicating direction information and command selections to processor 1604 and for controlling cursor movement on display 167. This input device typically has two degrees of freedom in two axes, a first axis (e.g., x) and a second axis (e.g., y), that allows the device to specify positions in a plane.

In some embodiments, the computer system 1600 can be used to perform various functions described herein. According to some embodiments, such use is provided by computer system 1600 in response to processor 1604 executing one or more sequences of one or more instructions contained in the main memory 1606. Those skilled in the art will know how to prepare such instructions based on the functions and methods described herein. Such instructions may be read into the main memory 1606 from another computer-readable medium, such as storage device 1610. Execution of the sequences of instructions contained in the main memory 1606 causes the processor 1604 to perform the process steps described herein. One or more processors in a multi-processing arrangement may also be employed to execute the sequences of instructions contained in the main memory 1606. In alternative embodiments, hard-wired circuitry may be used in place of or in combination with software instructions to implement the various embodiments described herein. Thus, embodiments are not limited to any specific combination of hardware circuitry and software.

The term "computer-readable medium" as used herein refers to any medium that participates in providing instructions to the processor 1604 for execution. Such a medium may take many forms, including but not limited to, non-volatile media, volatile media, and transmission media. Non-volatile media includes, for example, optical or magnetic disks, such as the storage device 1610. Volatile media includes dynamic memory, such as the main memory 1606. Transmission media includes coaxial cables, copper wire and fiber optics, including the wires that comprise the bus 1602. Transmission media can also take the form of acoustic or light waves, such as those generated during radio wave and infrared data communications.

Common forms of computer-readable media include, for example, a floppy disk, a flexible disk, hard disk, magnetic tape, or any other magnetic medium, a CD-ROM, any other optical medium, punch cards, paper tape, any other physical medium with patterns of holes, a RAM, a PROM, and EPROM, a FLASH-EPROM, any other memory chip or cartridge, a carrier wave as described hereinafter, or any other medium from which a computer can read.

Various forms of computer-readable media may be involved in carrying one or more sequences of one or more instructions to the processor 1604 for execution. For example, the instructions may initially be carried on a magnetic disk of a remote computer. The remote computer can load the instructions into its dynamic memory and send the instructions over a telephone line using a modem. A modem local to the computer system 1600 can receive the data on the telephone line and use an infrared transmitter to convert the data to an infrared signal. An infrared detector coupled to the bus 1602 can receive the data carried in the infrared signal and place the data on the bus 1602. The bus 1602 carries the data to the main memory 1606, from which the processor 1604 retrieves and executes the instructions. The instructions received by the main memory 1606 may optionally be stored on the storage device 1610 either before or after execution by the processor 1604.

The computer system 1600 also includes a communication interface 1618 coupled to the bus 1602. The communication interface 1618 provides a two-way data communication coupling to a network link 1620 that is connected to a local network 1622. For example, the communication interface 1618 may be an integrated services digital network (ISDN) card or a modem to provide a data communication connection to a corresponding type of telephone line. As another example, the communication interface 1618 may be a local area network (LAN) card to provide a data communication connection to a compatible LAN. Wireless links may also be implemented. In any such implementation, the communication interface 1618 sends and receives electrical, electromagnetic or optical signals that carry data streams representing various types of information.

The network link 1620 typically provides data communication through one or more networks to other devices. For example, the network link 1620 may provide a connection through local network 1622 to a host computer 1624 or to equipment 1626 such as a radiation beam source or a switch operatively coupled to a radiation beam source. The data streams transported over the network link 1620 can comprise electrical, electromagnetic or optical signals. The signals through the various networks and the signals on the network link 1620 and through the communication interface 1618, which carry data to and from the computer system 1600, are exemplary forms of carrier waves transporting the information. The computer system 1600 can send messages and receive data, including program code, through the network(s), the network link 1620, and the communication interface 1618.

Although particular features have been shown and described, it will be understood that they are not intended to limit the claimed invention, and it will be made obvious to those skilled in the art that various changes and modifications may be made without departing from the spirit and scope of the claimed invention. The specification and drawings are, accordingly to be regarded in an illustrative rather than restrictive sense. The claimed invention is intended to cover all alternatives, modifications and equivalents.

The invention claimed is:

1. A marker system, comprising:
a first marker;
a second marker, wherein the first marker and the second marker are configured to emit light from one or more light sources coupled to the first marker and the second marker, the light comprising invisible light for detection by a video camera;
a filter, wherein the filter is configured to filter out visible light while allowing the invisible light emitted by the first and second markers to pass therethrough for detection by the video camera to generate an image in response to the invisible light, the image being a part of a video generated by the video camera; and
a structure coupled to the first marker and/or the second marker, wherein the structure has a base and a surface that is oriented at an angle with respect to the base.

2. The marker system of claim 1, further comprising a first fiber optic configured to transmit light from the one or more light sources to the first marker, and a second fiber optic configured to transmit light from the one or more light sources to the second marker.

3. The marker system of claim 2, further comprising the one or more light sources.

4. The marker system of claim 3, wherein the one or more light sources comprise one LED at a LED unit.

5. The marker system of claim 3, wherein the one or more light sources comprise a plurality of LEDs at a LED unit.

6. The marker system of claim 1, wherein the structure comprises a marker block to which the first marker and the second marker are coupled.

7. The marker system of claim 6, further comprising the one or more light sources, wherein the one or more light sources are at the marker block.

8. The marker system of claim 6, further comprising the one or more light sources, wherein the one or more light sources are external to the marker block and are coupled to the marker block by an optical fiber cable.

9. The marker system of claim 6, wherein the first marker and the second marker are detachably coupled to the marker block.

10. The marker system of claim 6, wherein the first marker comprises a first LED, and the second marker comprises a second LED;
wherein the marker system further comprises a third marker having a third LED; and
wherein the first and the third LEDs have different respective half angles, the first marker is detachably coupled to the marker block at a first location, and the third marker is detachably coupled to the marker block at the first location when the first marker is detached from the marker block.

11. The marker system of claim 1, further comprising the one or more light sources.

12. The marker system of claim 11, wherein the one or more light sources comprise a first LED at the first marker, and a second LED at the second marker.

13. The marker system of claim 11, wherein one of the one or more light sources is configured to emit infrared light.

14. The marker system of claim 11, wherein one of the one or more light sources is configured to emit light having at least a wavelength of 365 nm.

15. The marker system of claim 11, wherein one of the one or more light sources is configured to emit visible light.

16. The marker system of claim 11, wherein one of the one or more light sources is configured to emit light having a wavelength that is anywhere from 500 nm to 700 nm.

17. The marker system of claim 11, wherein one of the one or more light sources has a half angle that is anywhere between 65° and 75°.

18. The marker system of claim 11, wherein one of the one or more light sources is configured to emit light continuously.

19. The marker system of claim 11, wherein one of the one or more light sources is configured to emit light in pulses.

20. The marker system of claim 1, further comprising the video camera for receiving light from the first marker and light from the second marker.

21. The marker system of claim 20, wherein the video camera comprises the filter.

22. The marker system of claim 1, wherein the filter is configured to reduce light being imaged by the video camera to a bandwidth anywhere within a range of 10 nm to 100 nm.

23. The marker system of claim 1, wherein the filter comprises a bandpass filter.

24. The marker system of claim 1, further comprising one or more neutral density filters for reducing ambient light intensity.

25. The marker system of claim 1, wherein the filter is part of a filter unit configure for reducing ambient light to a level that corresponds with a noise level of the video camera.

26. The marker system of claim 1, wherein the base is a first base and the first base has a first securing mechanism for detachably securing the first marker to an object; and
wherein the marker system further comprises an additional structure having a second base with a second securing mechanism for detachably securing the second marker to the object.

27. The marker system of claim 26, wherein the first securing mechanism comprises a first adhesive and a first cover covering the first adhesive, and the second securing mechanism comprises a second adhesive and a second cover covering the second adhesive.

28. A camera system for receiving and filtering light emitted from a first marker and a second marker, wherein the first marker and/or the second marker is coupled to a structure, wherein the structure has a base and a surface that is oriented at an angle with respect to the base, the camera system comprising:
a video camera configured for receiving light emitted from the first marker and light emitted from the second marker;
wherein the video camera comprises one or more filters for reducing ambient light to a level that corresponds with a noise level of the video camera while allowing the light emitted from the first and second markers to be imaged by the video camera, and wherein the one or more filters are configured to filter out visible light while allowing invisible light to pass therethrough for detection by the video camera to generate an image in response to the invisible light, the image being a part of a video generated by the video camera.

29. The camera system of claim 28, wherein the light emitted from the first marker and the light emitted from the second marker are generated by one or more LEDs at the first and second markers or coupled to the first and second markers by fiber optics.

30. The camera system of claim 28, wherein the one or more filters are configured to reduce light to a bandwidth anywhere within a range of 10 nm to 100 nm.

31. The camera system of claim 28, wherein the one or more filters comprise a bandpass filter.

32. The camera system of claim 28, wherein the one or more filters comprise one or more neutral density filters for reducing ambient light intensity.

33. The camera system of claim 28, wherein the one or more filters comprises one or a combination of a bandpass filter, high pass filter, low pass filter, and neutral density filter.

34. A method performed using a marker system, comprising:
generating light using one or more light sources;
emitting the light at a plurality of markers that are coupled to the light sources, the light comprising invisible light;
using one or more filters to filter out visible light while allowing the invisible light to pass therethrough for detection by a video camera to generate an image as a part of a video in response to the invisible light; and
detecting the invisible light emitted from the plurality of markers using the video camera;
wherein at least one of the markers is coupled to a structure, the structure having a base and a surface oriented at an angle with respect to the base.

35. The method of claim 34, wherein the one or more light sources comprise one or more LEDs.

36. The method of claim 34, further comprising transmitting the generated light from the one or more light sources to the plurality of markers.

37. The method of claim 34, wherein the one or more filters are configured to reduce light being imaged by the video camera to a bandwidth anywhere within a range of 10 nm to 100 nm.

38. The method of claim 34, wherein the act of using the one or more filters comprises using a bandpass filter.

39. The method of claim 34, wherein the act of using the one or more filters comprises using one or more neutral density filters for reducing ambient light intensity.

40. The method of claim 34, wherein the one or more filters comprises one or a combination of a bandpass filter, high pass filter, low pass filter, and neutral density filter.

41. The method of claim 34, further comprising determining a position of an object to which the markers are coupled based at least in part on the detected invisible light, wherein the act of determining the position is performed using a processor.

42. A marker system, comprising:
one or more support structure(s); and
a plurality of markers coupled to the one or more support structure(s);
wherein at least one of the plurality of markers is configured to absorb light at a first wavelength, and emit light at a second wavelength for detection outside a human subject, wherein the second wavelength is different from the first wavelength; and
wherein at least one of the one or more support structure(s) comprises a base and a surface that is oriented at a non-zero angle with respect to the base, the angle being an acute angle, and wherein the at least one of the plurality of markers is coupled to the surface of the at least one of the one or more support structure(s).

43. The marker system of claim 42, wherein the at least one of the plurality of markers comprises a fluorescent material.

44. The marker system of claim 43, wherein the fluorescent material comprises a TL-0156 fluorophore.

45. The marker system of claim 42, further comprising a video camera for detecting the light emitted from the at least one of the plurality of markers.

46. The marker system of claim 45, wherein the video camera comprises a light source configured to emit light at the first wavelength.

47. The marker system of claim 42, wherein at least one of the plurality of markers is configured to emit the light at the second wavelength in a form of an afterglow.

48. The marker system of claim 1, the angle being an acute angle.

49. The method of claim 1, the angle being 0°.

50. The marker system of claim 1, wherein the video is an invisible light-based video.

51. The camera system of claim 28, wherein the video is an invisible light-based video.

52. The method of claim 34, wherein the video is an invisible light-based video.

53. The marker system of claim 45, wherein the video camera is configured to generate invisible light-based video.

* * * * *